(12) United States Patent
Acton

(10) Patent No.: US 6,268,135 B1
(45) Date of Patent: Jul. 31, 2001

(54) PHOSPHOLIPASE MOLECULE AND USES THEREFOR

(75) Inventor: Susan Acton, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/163,833

(22) Filed: Sep. 30, 1998

(51) Int. Cl.[7] ............... C12Q 1/68; C12N 9/20; C12N 1/20; C12N 15/00; C07H 21/04

(52) U.S. Cl. ............ 435/6; 435/198; 435/252.3; 435/320.1; 435/21; 536/23.2; 536/23.5; 530/350

(58) Field of Search ............ 435/6, 21, 198, 435/252.3, 320.1; 536/23.2, 23.5; 530/350

(56) References Cited

PUBLICATIONS

Clark, J.D. et al. "Purification of a 110–kilodalton cytosolic phospholipase A2 from the human monocytic cell line U937" *Proc. Natl. Acad. Sci. U S A*. Oct. 1990; 87(19):7708–12.

Davidson, F.F. and E.A. Dennis "Evolutionary relationships and implications for the regulation of phospholipase A2 from snake venom to human secreted forms" *J. Mol. Evol.* Sep. 1990;31(3):228–38.

Genbank Accession No. P51452 for "Dual Specificity Protein Phosphatase 3 (Dual Specificity Protein Phosphatase VHR)".

Gomez, F. et al. "Purification and characterization of five variants of phospholipase A2 and complete primary structure of the main phospholipase A2 variant in Heloderma suspectum (Gila monster) venom" *Eur. J. Biochem.* Dec. 8, 1989;186(1–2):23–33.

Hazen, S.L. et al. "Purification and characterization of canine myocardial cytosolic phospholipase A2. A calcium–independent phospholipase with absolute f1–2 regiospecificity for diradyl glycerophospholipids" *J. Biol. Chem.* Jun. 25, 1990;265(18):10622–30.

Ishibashi, T. et al. "Expression cloning of a human dual–specificity phosphatase" *Proc. Natl. Acad. Sci. U S A*. Dec. 15, 1992;89(24):12170–4.

Kramer, R.M. et al. "Structure and properties of a human non–pancreatic phospholipase A2" *J Biol. Chem.* Apr 5, 1989;264(10):5768–75.

Leslie, C.C. et al. "Properties and purification of an arachidonoyl–hydrolyzing phospholipase A2 from a macrophage cell line, RAW 264.7" *Biochim. Biophys. Acta* Dec. 16, 1988;963(3):476–92.

Verheij, H.M. et al. "Structure and function of phospholipase A2" *Rev. Physiol. Biochem. Pharmacol.* 1981;91:91–203.

Yuvaniyama J, et al. "Crystal structure of the dual specificity protein phosphatase VHR" *Science* May 31, 1996;272(5266):1328–31.

*Primary Examiner*—Tekchand Saidha
(74) *Attorney, Agent, or Firm*—Lahive & Cockfield, LLP; Giulio A. DeConti, Jr.; Amy E. Mandragouras

(57) ABSTRACT

Novel CSAPL polypeptides, proteins, and nucleic acid molecules are disclosed. In addition to isolated, full-length CSAPL proteins, the invention further provides isolated CSAPL fusion proteins, antigenic peptides and anti-CSAPL antibodies. The invention also provides CSAPL nucleic acid molecules, recombinant expression vectors containing a nucleic acid molecule of the invention, host cells into which the expression vectors have been introduced and non-human transgenic animals in which a CSAPL gene has been introduced or disrupted. Diagnostic, screening and therapeutic methods utilizing compositions of the invention are also provided.

14 Claims, 3 Drawing Sheets fchrb018a01 cDNA sequence

GTCGACCCACGCGTCCGGAAGTGCACAGCCTGGGCCAGATACTCCCACAGGA
TGGACTCACTGCAGAAGCAGGACCTCCGGAGGCCCAAGATCCATGGGGCAGT
CCAGGCATCTCCCTACCAGCCGCCCACATTGGCTTCGCTGCAGCGCTTGCTGT
GGGTCCGTCAGGCTGCCACACTGAACCATATCGATGAGGTCTGGCCCAGCCT
CTTCCTGGGAGATGCGTACGCAGCCCGGGACAAGAGCAAGCTGATCCAGCTG
GGAATCACCCACGTTGTGAATGCCGCTGCAGGCAAGTTCCAGGTGGACACAG
GTGCCAAATTCTACCGTGGAATGTCCCTGGAGTACTATGGCATTGAGGCGGA
CGACAACCCCTTCTTCGACCTCAGTGTCTACTTTCTGCCTGTTGCTCGATACAT
CCGAGCTGCCCTCAGTGTTCCCCAAGGCCGCGTGCTGGTACACTGTGCCATGG
GGGTAAGCCGCTCTGCCACACTTGTCCTGGCCTTCCTCATGATCTATGAGAAC
ATGACGCTGGTAGAGGCCATCCAGACGGTGCAGGCCCACCGCAATATCTGCC
CTAACTCAGGCTTCCTCCGGCAGCTCCAGGTTCTGGACAACCGACTGGGGCG
GGAGACGGGGCGGTTCTGATCTGGCAGGCAGCCAGGATCCCTGACCCTTGGC
CCAACCCCACCAGCCTGGCCCTGGGAACAGCAGGCTCTGCTGTTTCTAGTGA
CCCTGAGATGTAAACAGCAAGTGGGGGCTGAGGCAGAGGCAGGGATAGCTG
GGTGGTGACCTCTTAGCGGGTGGATTTCCCTGACCCAATTCAGAGATTCTTTA
TGCAAAAGTGAGTTCAGTCCATCTCTATAATAAAATATTCATCGTCATAAAAA
AAAAAAAAAAAAGGGCGGCCGC

FIGURE 1

MDSLQKQDLRRPKIHGAVQASPYQPPTLASLQRLLWVRQAATLNHIDEVWPSLF
LGDAYAARDKSKLIQLGITHVVNAAAGKFQVDTGAKFYRGMSLEYYGIEADDN
PFFDLSVYFLPVARYIRAALSVPQGRVLVHCAMGVSRSATLVLAFLMIYENMTL
VEAIQTVQAHRNICPNSGFLRQLQVLDNRLGRETGRF*

FIGURE 2

```
ALIGN calculates a global alignment of two sequences
 version 2.0uPlease cite: Myers and Miller, CABIOS (1989)
> SwissProt p51452 - DUAL SPECIFICITY PROTEIN PHO    185 aa vs.
> fchrb018a01.aa                                    199 aa
scoring matrix: pam120.mat, gap penalties: -12/-4
37.3% identity;          Global alignment score: 219

10        20        30                         40
inputs  MSGSFELSVQDLNDLLSDGSGCYSLPSQPC---------------NEVTPRIYVGNASV
        :..    ...   .   .  ..  :   :. .              .::  :  ...:.:  .
        MDSLQKQDLRRPKIHGAVQASPYQPPTLASLQRLLWVRQAATLNHIDEVWPSLFLGDAYA
               10        20        30        40        50        60

50        60        70        80        90       100
inputs  AQDIPKLQKLGITHVLNAAEGRSFMHVNTNANFYKDSGITYLGIKANDTQEFNLSAYFER
        :.:  .::   .::::::.:::.:.   :   .:.:.:.:..  ..  :  ::  :.:..  :.::.::
        ARDKSKLIQLGITHVVNAAAGK-F-QVDTGAKFYRGMSLEYYGIEADDNPFFDLSVYFLP
               70        80        90       100       110

110       120       130       140       150       160
inputs  AADFIDQALAQKNGRVLVHCREGYSRSPTLVIAYLMMRQKMDVKSALSIVRQNREIGPND
        .:  .:   ::.    .::::::::   :  :::::.::..::.    ...:   .  :.   ..:.:   ::..
        VARYIRAALSVPQGRVLVHCAMGVSRSATLVLAFLMIYENMTLVEAIQTVQAHRNICPNS
              120       130       140       150       160       170

170       180
inputs  GFLAQLCQLNDRLAKEGKLKP
        :::  ::   :...:...:
        GFLRQLQVLDNRLGRETGRFN
              180       190
```

Fig. 3

PHOSPHOLIPASE MOLECULE AND USES THEREFOR

BACKGROUND OF THE INVENTION

Phospholipases are involved in the signaling pathway in which a cellular response such as proliferation or secretion is produced consequent to an extracellular stimulus. Activation of mammalian phosphoinositide-specific Phospholipase C (PLC) by a receptor-linked G-protein results in the hydrolysis of phosphatidylinositol-4,5-bisphosphate (PIP2) to release the second messengers 1,2-diacylglycerol (DAG) and 1,4,5-inositol trisphosphate (IP3). DAG activates protein kinase C (PKC), and IP3 releases calcium from stores in the endoplasmic reticulum. Sustained response to the stimulus arises from processing of phosphatidylcholine (PC) by either PLC, which generates DAG directly, or by PLC, which gives phosphatidic acid (PA); PA is then hydrolyzed to DAG.

Phospholipase A2 (PLA2) represents a class of heat-stable, calcium-dependent enzymes catalyzing the hydrolysis of the 2-acyl bond of 3-n-phosphoglycerides. This enzyme is named Phospholipase A2 to denote its 2-acyl specificity (Uthe 1971). Each protein is composed of dimeric subunits, α, β, respectively (Wells 1971). PLA2s hydrolyze the sn-2 ester bond on L-glycerophospholipids. At present there are three commonly recognized categories of PLA2s: a large (85 kDa) Ca++ dependent cytosolic PLA2 (Leslie et al: *Biochem Biophys. Acta* 963:476–492 (1988); Clark et al.: *Proc. Natl. Acad. Sci. USA* 87:7708–7712 (1990); Kramer et al. 1991), a smaller (40 kDa) Ca++ independent PLA2 found in myocardium (Hazen et al.: *J. Biol. Chem.* 265:10622–10630 (1990)), and a less well defined group of secreted enzymes found in platelets, synovial fluid, and in some insect and lizard venoms (Verheij et al.: *Rev. Physiol. Biochem. Phramacol.* 91:91–103 (1981); Dennis: *The Enzymes* 16:307–353 (1983); Kramer et al. *J. Biol. Chem.* 264:5768–5775 (1989)). BV-PLA2 is one of many PLA2s in it's class of small, secreted, Ca++ dependent PLA2 enzymes (Dawson: Chemical Studies of Structural Features in Staphylococcus Nuclease T', in *Form and Function of Phospholipids*, (Ansell, Hawthorne and Dawson eds.), Elsevier, Amsterdam, 97 (1973)).

The first cystolic forms of PLA2 have been implicated in the release of arachidonic acid from cell membranes. This release in arachidonic acid has been reported to be indirectly involved in the inflammatory response. Several types of PLA2s such as Secretory Phospholipase $A_2$, Phospholipase $A_2$, and Human Extracellular Group II Phospholipase $A_2$ are involved in inflammatory diseases such as Rheumatic disease, acute pancreatitis, and skin inflammation, respectively. Arachidonic acid in mast cells, macrophages, monocytes, eosinophils and basophils is released from membrane phospholipids by the activation of phospholipase A2. After its release, arachidonic acid undergoes metabolism via two major pathways: the cyclooxygenase pathway (which produces various prostaglandins and thromboxanes) and the 5-lipoxygenase pathway (which produces leukotrienes). Leukotrienes are "slow reacting substances of anaphylaxis" and have been named A, B, C, D, and E leukotrienes and these leukotrienes subtypes play a crucial role in asthma.

Phospholipases are targets of a variety of body system modulating agents one of which is endothelin, an endothelium derived vasoactive polypeptide which is the most potent vasoconstrictor identified to date. This protein modulates vascular smooth muscle tone as well as participating in the long term control of the cell cycle involved in the chronic remodeling of the vascular tree. Additionally, endothelin interacts with phospholipases via guanine nucleotide regulatory proteins using a common guanine nucleotide modulating machinery. Thus, phospholipases are an important component of the complex array of effectors which regulate the response of organs, such as the heart, to disease states and injury recovery.

Given the importance of such phospholipases in the regulation of lipid metabolism, signal transduction, and cell cycle control, there exists a need to identify novel phospholipases which function as modulators in these processes such as the suppression of inflammation and oncogenesis and whose aberrant function can result in disorders arising from improper signal transduction such as cancer, inappropriate levels of phospholipase metabolites which mediate the anaphalactic response in respiratory disorders such as asthma, as well as improper responses to disease states such as chronic heart failure which direct tissues into a remodeling paradigm. Further, phospholipases may be potential drug target candidates in a variety of disease areas, including anticancer drugs, cardiovascular drugs, and anti-inflammatory drugs.

SUMMARY OF THE INVENTION

The present invention is based, at least in part, on the discovery of novel nucleic acid molecules and proteins encoded by such nucleic acid molecules, refered herein as "Cardiovascular System Associated Phospholipase" ("CSAPL") proteins. The CSAPL nucleic acid and protein molecules of the present invention are useful as modulating agents in regulating a variety of cellular processes, e.g., cardiac cellular processes; lipid metabolism, e.g., release of arachidonic acid from cell membranes; inflammatory response. Accordingly, in one aspect, this invention provides isolated nucleic acid molecules encoding CSAPL proteins or biologically active portions thereof, as well as nucleic acid fragments suitable as primers or hybridization probes for the detection of CSAPL-encoding nucleic acids.

In one embodiment, a CSAPL nucleic acid molecule of the invention is at least 10%, 15%, 20%, 25%, 30%, 35%, 40%, 45%, 50%, 55%, 60%, 65%, 70%, 75%, 80%, 85%, 90%, 95%, 98%, 99%, or more homologous to a nucleotide sequence (e.g., to the entire length of the nucleotide sequence) including SEQ ID NO:1, SEQ ID NO:3 or a complement thereof.

In a preferred embodiment, the isolated nucleic acid molecule includes the nucleotide sequence shown SEQ ID NO:1 or SEQ ID NO:3, or a complement thereof. In another embodiment, the nucleic acid molecule includes SEQ ID NO:3 and nucleotides 1–690 of SEQ ID NO:1. In another preferred embodiment, the nucleic acid molecule has the nucleotide sequence shown in SEQ ID NO:1 or SEQ ID NO:3. In another preferred embodiment, the nucleic acid molecule comprises a fragment of at least 594 nucleotides of the nucleotide sequence of SEQ ID NO:1, SEQ ID NO:3 or a complement thereof In another embodiment, an CSAPL nucleic acid molecule includes a nucleotide sequence encoding a protein having an amino acid sequence sufficiently homologous to the amino acid sequence of SEQ ID NO:2. In a preferred embodiment, an CSAPL nucleic acid molecule includes a nucleotide sequence encoding a protein having an amino acid sequence at least 30%, 35%, 37%, 40%, 45%, 50%, 55%, 60%, 65%, 70%, 75%, 80%, 85%, 90%, 95%, 98% or more homologous to the amino acid sequence of SEQ ID NO:2.

In another preferred embodiment, an isolated nucleic acid molecule encodes the amino acid sequence of human CSAPL. In yet another preferred embodiment, the nucleic acid molecule includes a nucleotide sequence encoding a protein having the amino acid sequence of SEQ ID NO: 2. In yet another preferred embodiment, the nucleic acid molecule is at least 594 nucleotides in length. In a further preferred embodiment, the nucleic acid molecule is at least 594 nucleotides in length and encodes a protein having an CSAPL activity (as described herein).

Another embodiment of the invention features nucleic acid molecules, preferably CSAPL nucleic acid molecules, which specifically detect CSAPL nucleic acid molecules relative to nucleic acid molecules encoding non-CSAPL proteins. For example, in one embodiment, such a nucleic acid molecule is at least 350, 400, 450, 500, 550, 593, 600, 650, 700, 750, or 800 nucleotides in length and hybridizes under stringent conditions to a nucleic acid molecule comprising the nucleotide sequence shown in SEQ ID NO:1, or a complement thereof. In a particularly preferred embodiment, the nucleic acid molecule comprises a fragment of at least 594 nucleotides of the nucleotide sequence of SEQ ID NO:1, SEQ ID NO:3, or a complement thereof. In preferred embodiments, the nucleic acid molecules are at least 15 (e.g., contiguous) nucleotides in length and hybridize under stringent conditions to nucleotides 37–630 of SEQ ID NO:1. In other preferred embodiments, the nucleic acid molecules include nucleotides 37–630 of SEQ ID NO:1.

In other preferred embodiments, the nucleic acid molecule encodes a naturally occurring allelic variant of a polypeptide which includes the amino acid sequence of SEQ ID NO:2, wherein the nucleic acid molecule hybridizes to a nucleic acid molecule which includes SEQ ID NO:1 or SEQ ID NO:3 under stringent conditions.

Another embodiment of the invention provides an isolated nucleic acid molecule which is antisense to a CSAPL nucleic acid molecule, e.g., the coding strand of a CSAPL nucleic acid molecule.

Another aspect of the invention provides a vector comprising a CSAPL nucleic acid molecule. In certain embodiments, the vector is a recombinant expression vector. In another embodiment, the invention provides a host cell containing a vector of the invention. The invention also provides a method for producing a protein, preferably a CSAPL protein, by culturing in a suitable medium, a host cell, e.g., a mammalian host cell such as a non-human mammalian cell, of the invention containing a recombinant expression vector, such that the protein is produced.

Another aspect of this invention features isolated or recombinant CSAPL proteins and polypeptides. In one embodiment, the isolated protein, preferably a CSAPL protein, includes a CSAPL unique N-terminal domain, at least one Phospholipase $A_2$ active site, and a CSAPL unique C-terminal domain.

In another embodiment, the isolated protein preferably includes a CSAPL unique N-terminal domain, at least one Phospholipase $A_2$ active site, and a CSAPL unique C-terminal domain and has an amino acid sequence which is at least 35%, 37%, 40%, 45%, 50%, 55%, 60%, 65%, 70%, 75%, 80%, 85%, 90%, 95%, 99% or more homologous to an amino acid sequence including SEQ ID NO:2. In yet another embodiment, the isolated protein, preferably a CSAPL protein, includes a CSAPL unique N-terminal domain, at least one Phospholipase $A_2$ active site, and a CSAPL unique C-terminal domain and is expressed and/or functions in cells of the cardiovascular system. In an even further embodiment, the isolated protein, preferably a CSAPL protein, includes a CSAPL unique N-terminal domain, at least one Phospholipase $A_2$ active site, and a CSAPL unique C-terminal domain and plays a role in signalling pathways associated with cellular growth, e.g., signalling pathways associated with cell cycle regulation. In another embodiment, the isolated protein, preferably a CSAPL protein, includes a CSAPL unique N-terminal domain, at least one Phospholipase $A_2$ active site, and a CSAPL unique C-terminal domain and is encoded by a nucleic acid molecule having a nucleotide sequence which hybridizes under stringent hybridization conditions to a nucleic acid molecule comprising the nucleotide sequence of SEQ ID NO:1 or SEQ ID NO:3.

In another embodiment, the isolated protein, preferably a CSAPL protein, has an amino acid sequence sufficiently homologous to the amino acid sequence of SEQ ID NO:2. In a preferred embodiment, the protein, preferably a CSAPL protein, has an amino acid sequence at least about 35%, 37%, 40%, 45%, 50%, 55%, 60%, 65%, 70%, 75%, 80%, 85%, 90%, 95%, 99% or more homologous to an amino acid sequence including SEQ ID NO:2 (e.g., the entire amino acid sequence of SEQ ID NO:2). In another embodiment, the invention features fragments of the proteins having the amino acid sequence of SEQ ID NO:2, wherein the fragment comprises at least 15 amino acids (e.g., contiguous amino acids) of the amino acid sequence of SEQ ID NO:2. In another embodiment, the protein, preferably a CSAPL protein, has the amino acid sequence of SEQ ID NO:2.

Another embodiment of the invention features an isolated protein, preferably a CSAPL protein, which is encoded by a nucleic acid molecule having a nucleotide sequence at least about 10%, 15%, 20%, 25%, 30%, 35%, 40%, 45%, 50%, 55%, 60%, 65%, 70%, 75%, 80%, 85%, 90%, 95%, 98%, 99%, or more homologous to a nucleotide sequence (e.g., to the entire length of the nucleotide sequence) including SEQ ID NO:1, SEQ ID NO:3, or a complement thereof. This invention further features an isolated protein, preferably a CSAPL protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, or a complement thereof.

The proteins of the present invention or portions thereof, e.g., biologically active portions thereof, can be operatively linked to a non-CSAPL polypeptide (e.g., heterologous amino acid sequences) to form fusion proteins. The invention further features antibodies, such as monoclonal or polyclonal antibodies, that specifically bind proteins of the invention, preferably CSAPL proteins. In addition, the CSAPL proteins or biologically active portions thereof can be incorporated into pharmaceutical compositions, which optionally include pharmaceutically acceptable carriers.

In another aspect, the present invention provides a method for detecting the presence of a CSAPL nucleic acid molecule, protein or polypeptide in a biological sample by contacting the biological sample with an agent capable of detecting a CSAPL nucleic acid molecule, protein or polypeptide such that the presence of a CSAPL nucleic acid molecule, protein or polypeptide is detected in the biological sample.

In another aspect, the present invention provides a method for detecting the presence of CSAPL activity in a biological sample by contacting the biological sample with an agent capable of detecting an indicator of CSAPL activity such that the presence of CSAPL activity is detected in the biological sample.

In another aspect, the invention provides a method for modulating CSAPL activity comprising contacting a cell capable of expressing CSAPL with an agent that modulates CSAPL activity such that CSAPL activity in the cell is modulated. In one embodiment, the agent inhibits CSAPL activity. In another embodiment, the agent stimulates CSAPL activity. In one embodiment, the agent is an antibody that specifically binds to a CSAPL protein. In another embodiment, the agent modulates expression of CSAPL by modulating transcription of a CSAPL gene or translation of a CSAPL mRNA. In yet another embodiment, the agent is a nucleic acid molecule having a nucleotide sequence that is antisense to the coding strand of a CSAPL mRNA or a CSAPL gene.

In one embodiment, the methods of the present invention are used to treat a subject having a disorder characterized by aberrant CSAPL protein or nucleic acid expression or activity by administering an agent which is a CSAPL modulator to the subject. In one embodiment, the CSAPL modulator is a CSAPL protein. In another embodiment the CSAPL modulator is a CSAPL nucleic acid molecule. In yet another embodiment, the CSAPL modulator is a peptide, peptidomimetic, or other small molecule. In a preferred embodiment, the disorder characterized by aberrant CSAPL protein or nucleic acid expression is a respiratory disorder, e.g., asthma, for example, anaphylaxis; inflammatory disease, e.g., Rheumatic Disease, Skin Inflammation, and Acute Pancreatitis; a cardiovascular disorder, e.g., congestive heart failure, or a disorder arising from improperly regulated phospholipase actions on lipids giving rise to improperly balanced amounts of lipid metabolites.

The present invention also provides a diagnostic assay for identifying the presence or absence of a genetic alteration characterized by at least one of (i) aberrant modification or mutation of a gene encoding a CSAPL protein; (ii) misregulation of the gene; and (iii) aberrant post-translational modification of a CSAPL protein, wherein a wild-type form of the gene encodes a protein with a CSAPL activity.

In another aspect the invention provides a method for identifying a compound that binds to or modulates the activity of a CSAPL protein, by providing an indicator composition comprising a CSAPL protein having CSAPL activity, contacting the indicator composition with a test compound, and determining the effect of the test compound on CSAPL activity in the indicator composition to identify a compound that modulates the activity of a CSAPL protein.

Other features and advantages of the invention will be apparent from the following detailed description and claims.

BRIEF DESCRIPTION OF THE DRAWINGS

FIG. 1 depicts the cDNA sequence of human CSAPL. The nucleotide sequence corresponds to nucleic acids 1 to 900 of SEQ ID NO:1.

FIG. 2 depicts the predicted amino acid sequence of human CSAPL. The amino acid sequence corresponds to amino acids 13–210 of SEQ ID NO:2. The coding region without the 5' and 3' untranslated regions of the human CSAPL gene is shown in SEQ ID NO:3.

FIG. 3 depicts the alignment between the human CSAPL amino acid sequence and dual specificity protein phosphatase (SwissProt No: P51452) amino acid sequence. This alignment were generated utilizing the ALIGN program with the following parameter setting: PAM120, gap penalties: −12/−4 (Myers, E. and Miller, W. (1988) "Optimal Alignments in Linear Space" CABIOS 4:11–17).

DETAILED DESCRIPTION OF THE INVENTION

The present invention is based, at least in part, on the discovery of novel molecules, referred to herein as "Cardiovascular System Associated Phospholipase" or "CSAPL" nucleic acid and polypeptide molecules, which play a role in or function in a variety of cellular processes, e.g., cardiac cellular processes; lipid metabolism, e.g., release of arachidonic acid from cell membranes; inflammatory response; second messenger pathways. In one embodiment, the CSAPL molecules of the present invention modulate the activity of one or more proteins involved in a proliferative disorder, e.g., cancer. In another embodiment, the CSAPL molecules of the present invention modulate the activity of one or more proteins involved in an immune cell disorder. In one embodiment, the CSAPL molecules of the present invention modulate the activity of one or more proteins involved in a cardiovascular disorder, e.g., congestive heart failure.

As used herein, the term "Phospholipase $A_2$" or "PLA2" includes an enzyme which is activated by binding a $Ca^{2+}$ ion and is capable of releasing fatty acids from the second carbon group of glycerol. Typically, a PLA2 catalytic domain includes side chains of two conserved residues, a histidine and an aspartic acid, participating in the catalytic domain. Phospholipase $A_2$s are small, rigid proteins of about 90–150 amino acid residues in length, typically 120 amino acid residues in length, including four to seven disulfide bonds. There are at least four forms of Phospholipase $A_2$s: pancreatic, membrane-associated as well as two less characterized forms. The venom of most snakes contains multiple forms of Phospholipase $A_2$s, and some of them are presynaptic neurotoxins which inhibit neuromuscular transmission by blocking acetylcholine release from the nerve termini (Davison and Dennis (1990) *J Mol Evol* 31:228–238; Gomez et al (1989) *Eur J Biochem* 186:23–33).

As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) *American Family Physician* 57:1901–04, the contents of which are incorporated herein by reference.

As used herein, the term "cardiac cellular processes" includes intra-cellular or inter-cellular processes involved in the functioning of the heart. Cellular processes involved in the nutrition and maintenance of the heart, the development of the heart, or the ability of the heart to pump blood to the rest of the body are intended to be covered by this term. Such processes include, for example, cardiac muscle contraction, distribution and transmission of electrical impulses, and cellular processes involved in the opening and closing of the cardiac valves. The term "cardiac cellular processes" further includes processes such as the transcription, translation and post-translational modification of proteins involved in the functioning of the heart, e.g., myofilament specific proteins, such as troponin I, troponin T, myosin light chain 1 (MLC1), and α-actinin.

One embodiment of the invention features CSAPL nucleic acid molecules, preferably human CSAPL molecules, which were identified from cDNA libraries made from hearts of patients with congestive heart failure (CHF) of ischemic and idiopathic origin. The CSAPL nucleic acid and protein molecules of the invention are described in further detail in the following subsections.

Another embodiment of the invention features CSAPL proteins and nucleic acid molecules which have sequence similarity with Phospholipase $A_2$s. Accordingly, CSAPL polypeptides of the invention may interact with (e.g., bind to) at least one ligand which is a phospholipid and, thus, may be involved in the regulation of proliferation, anti-proliferative mechanisms, lipid metabolism, inflammatory responses, and cardiac cellular processes.

In yet another embodiment, the isolated proteins of the present invention, preferably CSAPL proteins, are identified based on the presence of a CSAPL unique N-terminal domain, at least one phospholipase $A_2$ active site, and a CSAPL unique C-terminal domain. As used herein, a "CSAPL unique N-terminal domain" includes a protein domain which is at least about 95–135 amino acid residues in length, preferably at least 100–130 amino acid residues in length, more preferably at least 105–125, or at least 110–120, or preferably 117 amino acid residues in length. In another embodiment, a CSAPL unique N-terminal domain has at least 65–95%, preferably at least 70–90%, and more preferably at least 75–85% homology with the amino acid sequence of a CSAPL unique N-terminal domain of a human CSAPL sequence set forth in SEQ ID NO:2 (e.g., amino acid residues 13–130 of the amino acid sequence as set forth in SEQ ID NO:2). As further defined herein, a CSAPL unique N-terminal domain of a CSAPL protein family member, however, is not sufficiently homologous to the amino acid sequence of a member of another protein family, such as a non-CSAPL protein family. In a preferred embodiment, a CSAPL unique N-terminal domain has amino acid residues 13–130 of SEQ ID NO:2.

In another embodiment of the invention, a CSAPL family member is identified based on the presence of a phospholipase $A_2$ active site. As used herein, a "phospholipase $A_2$ active site" includes a protein domain which is at least 4–12 amino acid residues in length, preferably at least 5–11 amino acid tesidues in length, and more preferably at least 6–10, or at least 7–9, or preferably 8 amino acid residues in length, and is capable of binding a calcium ion to thereby release fatty acids from the second carbon group of glycerol of a phospholipid.

Preferably, a phospholipase $A_2$ active site includes the following amino acid consensus sequence (C-C-X (2)-H-X (2)-C, X=any amino acid). A phospholipase $A_2$ active site is capable of facilitating (e.g., catalyzing) the release of fatty acids from the second carbon group of glycerol of a phospholipid In one embodiment, a phospholipase $A_2$ active site has at least 65–95%, preferably at least 70–90%, and more preferably at least 75–85% homology with the amino acid sequence of a phospholipase $A_2$ active site of a human CSAPL sequence set forth in SEQ ID NO:2. In another embodiment, a phospholipase $A_2$ active site has amino acid residues 131–138 of the amino acid sequence as set forth in SEQ ID NO:2. Phospholipase $A_2$ active site are described in, for example, Davison and Dennis (1990) *J Mol Evol* 31:228–238 and Gomez et al (1989) *Eur J Biochem* 186:23–33, the contents of which are incorporated herein by reference. As further defined herein, a phospholipase $A_2$ active site of a CSAPL protein family member, however, is not sufficiently homologous to the amino acid sequence of a member of another protein family, such as a non-CSAPL protein family.

In another embodiment of the invention, a CSAPL family member is identified based on the presence of a CSAPL unique C-terminal domain. As used herein, a "CSAPL unique C-terminal domain" includes a protein domain which is at least 55–90 amino acid residues in length, preferably at least 60–85 amino acid residues in length, more preferably at least 65–80, or at least 70–75, or preferably 72 amino acid residues in length. In another embodiment, a CSAPL unique C-terminal domain has at least 65–95%, preferably at least 70–90%, and more preferably at least 75–85% homology with the amino acid sequence of a CSAPL unique C-terminal domain of a human CSAPL sequence set forth in SEQ ID NO:2 (e.g., amino acid residues 139–210 of the amino acid sequence as set forth in SEQ ID NO:2). As further defined herein, a CSAPL unique C-terminal domain of a CSAPL protein family member, however, is not sufficiently homologous to the amino acid sequence of a member of another protein family, such as a non-CSAPL protein family. In a preferred embodiment, a CSAPL unique C-terminal domain has amino acid residues 139–210 of SEQ ID NO:2.

In another embodiment, CSAPL family members include at least 1, 2, 3, 4 or more Protein kinase C (PKC) phosphorylation sites. PKC phosphorylation sites can be found at least within the amino acid sequence 13–210 of SEQ ID NO:2.

CSAPL family members can frther include at least 1 or more Casein kinase II phosphorylation sites. Casein kinase II phosphorylation sites can be found at least within the amino acid sequence 173–176 of SEQ ID NO:2.

CSAPL family members can flirther include at least 1 or more N-glycosylation sites. N-glycosylation sites can be found at least within the amino acid sequence 171–174 of SEQ ID NO:2. CSAPL family members can further include at least 1, 2 or more N-myristoylation sites. N-myristoylation sites can be found at least within the amino acid sequence 28–33 and 154–159 of SEQ ID NO:2. Wherein the site(s) have a consensus sequence selected from: [ST]-X-[RK], where S or T is a phosphorylation site; [RK]-X (2)-[DE]-X (3)-Y (see PROSITE document for alternative consensus sequences); N-{P}-[ST]-{P}, where N is a glycosylation site; G-{EDRKHPFYW}-X (2)-[STAGCN]-{P}, where G is an N-myristoylation site; and [ST]-X (2)-[DE], where S or T is a phosphorylation site, respectively. X designates any amino acid; (n) designates an alphanumeric number of "n" amino acids. These sites are further described in PROSITE Documents, Accession No. PDOC00005, PDOC00001, PDOC00008, PDOC00006, respectively (http://expasy.hcuge.ch/cgi-bin/get-prodoc-entry?PDOC00005, PDOC00001, PDOC00008, PDOC00006, respectively) and as PROSITE Accession No. PS00005, PS00001, PS00008, PS00006, respectively.

Isolated proteins of the present invention, preferably CSAPL proteins, have an amino acid sequence sufficiently homologous to the amino acid sequence of SEQ ID NO:2 or are encoded by a nucleotide sequence which includes a nucleotide sequence sufficiently homologous to SEQ ID NO:1, SEQ ID NO:3. As used herein, the term "sufficiently homologous" includes a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common finctional activity. For example, amino acid or nucleotide sequences which share common structural domains have at least 30–40% homology, preferably 40–50% homology, more preferably 50–60%, and even more preferably 60–70%, 70–80%, or 80–90% homology across the amino acid sequences of the domains and contain at least one and preferably two structural domains or motifs, are defined herein as sufficiently homologous. Furthermore, amino acid or nucleotide sequences which share at least 30–40%, preferably 40–50%, more preferably 50–60%, 60–70%, 70–80%, or 80–90% homology and share a common functional activity are defined herein as sufficiently homologous.

Accordingly, another embodiment of the invention features isolated CSAPL proteins and polypeptides having a CSAPL activity. Preferred proteins are CSAPL proteins having at least a CSAPL unique N-terminal domain, at least one phospholipase $A_2$ active site. Other preferred proteins are CSAPL proteins having at least a CSAPL unique N-terminal domain, at least one phospholipase $A_2$ active site, and a CSAPL unique C-terminal domain. Other preferred proteins are CSAPL proteins having at least a CSAPL unique N-terminal domain, and a CSAPL unique C-terminal domain. Other preferred proteins are CSAPL proteins having at least one phospholipase $A_2$ active site, and a CSAPL unique C-terminal domain.

The nucleotide sequence of the isolated human CSAPL cDNA and the predicted amino acid sequence of the human CSPATP polypeptide are shown in FIG. 1 and in SEQ ID NOs:1, 3 and 2, respectively.

The CSAPL gene, which is approximately 900 nucleotides in length, encodes a protein having a molecular weight of approximately 21.5 kD and which is approximately 197 amino acid residues in length. CSAPL message was detected in human heart and skeletal, in several rat tissues but predominantly in rat brain.

In a preferred embodiment, CSAPL proteins of the invention have an amino acid sequence of about 140–240, more preferably about 160–220, and even more preferably about 180–200 or 197 amino acid residues in length.

As used interchangeably herein, a "CSAPL activity", "biological activity of CSAPL" or "finctional activity of CSAPL", includes an activity exerted by a CSAPL protein, polypeptide or nucleic acid molecule as determined in vivo, in vitro, or in situ, according to standard techniques. In one embodiment, a CSAPL activity is a direct activity, such as an association with a CSAPL-target molecule. As used herein, a "target molecule" is a molecule with which a CSAPL protein binds or interacts in nature, such that CSAPL-mediated finction is achieved. A CSAPL target molecule can be a CSAPL protein or polypeptide of the present invention or a non-CSAPL molecule. For example, a CSAPL target molecule can be a non-CSAPL protein molecule. Alternatively, a CSAPL activity is an indirect activity, such as an activity mediated by interaction of the CSAPL protein with a CSAPL target molecule such that the target molecule modulates a downstream cellular activity (e.g., interaction of an CSAPL molecule with a CSAPL target molecule can modulate the activity of that target molecule on an immune cell).

In a preferred embodiment, a CSAPL activity is at least one or more of the following activities: (i) interaction of a CSAPL protein with a CSAPL target molecule; (ii) interaction of a CSAPL protein with a CSAPL target molecule, wherein the CSAPL target is a ligand, e.g., the 2-acyl bond of 3-n-phosphoglycerides.

In yet another preferred embodiment, a CSAPL activity is at least one or more of the following activities: (1) regulation of cell cycle, e.g., modulation of signal transduction, e.g., hydrolysis of phosphatidylinositol-4,5-bisphosphate (PIP2) to release the second messengers 1,2-diacylglycerol (DAG) (e.g., DAG activates protein kinase C (PKC)) and 1,4,5-inositol trisphosphate (IP3) (e.g., IP3 releases calcium from stores in the endoplasmic reticulum); (2) modulation of the inflammatory response, e.g., hydrolysis of the 2-acyl bond of 3-n-phosphoglycerides to produce arachidonic acid which is then processed into other molecules, e.g., leukotrienes, which mediate the induction of the inflammatory response.

Various aspects of the invention are described in further detail in the following subsections:

I. Isolated Nucleic Acid Molecules

One aspect of the invention pertains to isolated nucleic acid molecules that encode CSAPL proteins or biologically active portions thereof, as well as nucleic acid fragments sufficient for use as hybridization probes to identify CSAPL-encoding nucleic acids (e.g., CSAPL mRNA) and fragments for use as PCR primers for the amplification or mutation of CSAPL nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from chromosomal DNA, e.g., other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CSAPL nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or SEQ ID NO:3, or a portion thereof, can be isolated using standard molecular biology techniques and the sequence information provided herein. For Example, using all or portion of the nucleic acid sequence of SEQ ID NO:1 or SEQ ID NO:3, as a hybridization probe, CSAPL nucleic acid molecules can be isolated using standard hybridization and cloning techniques (e.g., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, or SEQ ID NO:3, can be isolated by the polymerase chain reaction (PCR) using synthetic oligonucleotide primers designed based upon the sequence of SEQ ID NO:1, or SEQ ID NO:3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CSAPL nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1, corresponds to the human CSAPL. This cDNA comprises sequence encoding the human CSAPL, protein (i.e., "the coding region", from nucleotides 37–630), 5' untranslated (from nucleotides 1–36) and 3' untranslated sequences (nucleotides 631–900). Alternatively, the nucleic acid molecule can comprise only the coding region of SEQ ID NO:1 (e.g., nucleotides 37–630, corresponding to SEQ ID NO:3).

In another preferred embodiment, an isolated nucleic acid molecule of the invention comprises a nucleic acid molecule which is a complement of the nucleotide sequence shown in SEQ ID NO:1, or SEQ ID NO:3 or a portion of any of these nucleotide sequences. A nucleic acid molecule which is complementary to the nucleotide sequence shown in SEQ ID NO:1, or SEQ ID NO:3, is one which is sufficiently complementary to the nucleotide sequence shown in SEQ ID NO:1, or SEQ ID NO:3, such that it can hybridize to the nucleotide sequence shown in SEQ ID NO:1, or SEQ ID NO:3, thereby forming a stable duplex.

In still another preferred embodiment, an isolated nucleic acid molecule of the present invention comprises a nucleotide sequence which is at least about 35%, preferably about 35–36%, 36–40%, more preferably at least about 40–42%, 42–45%, more preferably at least about 45–50%, and even more preferably at least about 50–55%, 55–57%, 57–60%, 60–65%, 65–70%, 70–75%, 75–80%, 80–85%, 85–90%, or 90–95% or more homologous to the nucleotide sequences shown in SEQ ID NO:1, or SEQ ID NO:3, or a portion of any of these nucleotide sequences.

Moreover, the nucleic acid molecule of the invention can comprise only a portion of the nucleic acid sequence (e.g., to the entire length of the nucleotide sequence) of SEQ ID NO:1, or SEQ ID NO:3, for example a fragment which can be used as a probe or primer or a fragment encoding a biologically active portion of a CSAPL protein. The nucleotide sequence determined from the cloning of the CSAPL gene allows for the generation of probes and primers designed for use in identifying and/or cloning other CSAPL family members, as well as CSAPL homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, or SEQ ID NO:3, of an anti-sense sequence of SEQ ID.NO:1, or SEQ ID NO:3, or of a naturally occurring mutant of SEQ ID NO:1, or SEQ ID NO:3.

In an exemplary embodiment, a nucleic acid molecule of the present invention comprises a nucleotide sequence which is about 100, preferably 100–200, preferably 200–300, more preferably 300–400, more preferably 400–500, more preferably 500–590, and even more preferably 590–594 nucleotides in length and hybridizes under stringent hybridization conditions to a nucleic acid molecule of SEQ ID NO:1, or SEQ ID NO:3.

Probes based on the CSAPL nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a CSAPL protein, such as by measuring a level of a CSAPL-encoding nucleic acid in a sample of cells from a subject e.g., detecting CSAPL mRNA levels or determining whether a genomic CSAPL gene has been mutated or deleted.

A nucleic acid fragment encoding a "biologically active portion of a CSAPL protein" can be prepared by isolating a portion of the nucleotide sequence of SEQ ID NO:1, or SEQ ID NO:3, which encodes a polypeptide having a CSAPL biological activity (the biological activities of the CSAPL proteins have previously been described), expressing the encoded portion of the CSAPL protein (e.g., by recombinant expression in vitro) and assessing the activity of the encoded portion of the CSAPL protein.

The invention further encompasses nucleic acid molecules that differ from the nucleotide sequence shown in SEQ ID NO:1, or SEQ ID NO:3, due to degeneracy of the genetic code and thus encode the same CSAPL proteins as those encoded by the nucleotide sequence shown in SEQ ID NO:1, SEQ ID NO:3. In another embodiment, an isolated nucleic acid molecule of the invention has a nucleotide sequence encoding a protein having an amino acid sequence shown in SEQ ID NO:2.

In addition to the CSAPL nucleotide sequences shown in SEQ ID NO:1, SEQ ID NO:3, it will be appreciated by those skilled in the art that DNA sequence polymorphisms that lead to changes in the amino acid sequences of the CSAPL proteins may exist within a population (e.g., the human population). Such genetic polymorphism in the CSAPL genes may exist among individuals within a population due to natural allelic variation. As used herein, the terms "gene" and "recombinant gene" refer to nucleic acid molecules isolated from chromosomal DNA, which include an open reading frame encoding an CSAPL protein, preferably a mammalian CSAPL protein. A gene includes coding DNA sequences, non-coding regulatory sequences, and introns. As used herein, a gene refers to an isolated nucleic acid molecule, as defined herein.

Allelic variants of human CSAPL include both functional and non-functional CSAPL proteins. Functional allelic variants are naturally occurring amino acid sequence variants of the human CSAPL protein that maintain the ability to bind an CSAPL ligand and/or modulate programmed cell death. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of the human CSAPL protein that do not have the ability to either bind an CSAPL ligand and/or modulate programmed cell death. Non-functional allelic variants will typically contain a non-conservative substitution, a deletion, or insertion or premature truncation of the amino acid sequence of SEQ ID NO:2 or a substitution, insertion or deletion in critical residues or critical regions.

The present invention further provides non-human orthologues of the human CSAPL protein. Orthologues of the human CSAPL protein are proteins that are isolated from non-human organisms and possess the same CSAPL ligand binding and/or modulation of programmed cell death capabilities of the human CSAPL protein. Orthologues of the human CSAPL protein can readily be identified as comprising an amino acid sequence that is substantially homologous to SEQ ID NO:2.

Moreover, nucleic acid molecules encoding other CSAPL family members (e.g., CSAPL-2), and thus which have a nucleotide sequence which differs from the CSAPL sequences of SEQ ID NO:1, or SEQ ID NO:3 are intended to be within the scope of the invention. For example, a CSAPL cDNA can be identified based on the nucleotide sequence of human CSAPL. Moreover, nucleic acid molecules encoding CSAPL proteins from different species, and thus which have a nucleotide sequence which differs from the CSAPL sequences of SEQ ID NO:1, or SEQ ID NO:3 are intended to be within the scope of the invention. For example, an mouse CSAPL cDNA can be identified based on the nucleotide sequence of a human CSAPL.

Nucleic acid molecules corresponding to natural allelic variants and homologues of the CSAPL cDNAs of the invention can be isolated based on their homology to the CSAPL nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, or SEQ ID NO:3. In other embodiment, the nucleic acid is at least 30, 50, 100, 250, 500, 550, or 600 nucleotides in length. As used herein, the term "hybridizes under stringent conditions" is intended to describe conditions for hybridization and washing under which nucleotide sequences at least about 10%, 15%, 20%, 25%, 30%, 35%, 40%, 45%, 50%, 55%, 60%, 65%, 70%, 75%, 80%, 85%, 90%, 95%, 98%, 99% or more homologous to each other typically remain hybridized to each other. Preferably, the conditions are such that sequences at least about 10%, at least about 20%, at least about 30%, at least about 40%, at least about 50%, at least about 60%, at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CSAPL sequences that may exist in the population, the skilled artisan will further appreciate that changes can be introduced by mutation into the nucleotide sequences of SEQ ID NO:1, or SEQ ID NO:3, thereby leading to changes in the amino acid sequence of the encoded CSAPL proteins, without altering the functional ability of the CSAPL proteins. For example, nucleotide substitutions leading to amino acid substitutions at "non-essential" amino acid residues can be made in the sequence of SEQ ID NO:1, or SEQ ID NO:3. A "non-essential" amino acid residue is a residue that can be altered from the wild-type sequence of CSAPL (e.g., the sequence of SEQ ID NO:2) without altering the biological activity, whereas an "essential" amino acid residue is required for biological activity. For example, amino acid residues that are conserved among the CSAPL proteins of the present invention, are predicted to be particularly unamenable to alteration (e.g., the three cysteines involved in disulfide bonds and the conserved histidine involved in forming the active enzymatic site). Moreover, amino acid residues that are defined by the CSAPL unique N-terminal domain, the phospholipase A$_2$ active site, and the CSAPL unique C-terminal domain are particularly unamenable to alteration. Furthermore, additional amino acid residues that are conserved between the CSAPL proteins of the present invention and other members of the phospholipase superfamily or protein families containing phospholipase activity are not likely to be amenable to alteration.

Accordingly, another aspect of the invention pertains to nucleic acid molecules encoding CSAPL proteins that contain changes in amino acid residues that are not essential for activity. Such CSAPL proteins differ in amino acid sequence from SEQ ID NO:2 yet retain biological activity. In one embodiment, the isolated nucleic acid molecule comprises a nucleotide sequence encoding a protein, wherein the protein comprises an amino acid sequence at least about 20%, 25%, 30%, 35%, 37%, 40%, 45%, 48%, 50%, 55%, 60%, 65%, 70%, 75%, 80%, 85%, 90%, 95% or more homologous to the amino acid sequence of SEQ ID NO:2. Preferably, the protein encoded by the nucleic acid molecule is at least about 65–70% homologous to SEQ ID NO:2, more preferably at least about 75–80% homologous to SEQ ID NO:2, even more preferably at least about 85–90% homologous to SEQ ID NO:2, and most preferably at least about 95% homologous to SEQ ID NO:2 (e.g., the entire amino acid sequence of SEQ ID NO:2).

An isolated nucleic acid molecule encoding a CSAPL protein homologous to the protein of SEQ ID NO:2 can be created by introducing one or more nucleotide substitutions, additions or deletions into the nucleotide sequence of SEQ ID NO:1, or SEQ ID NO:3, such that one or more amino acid substitutions, additions or deletions are introduced into the encoded protein. Mutations can be introduced into SEQ ID NO:1, SEQ ID NO:3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a CSAPL protein is preferably replaced with another amino acid residue from the same side chain family. Alternatively, in another embodiment, mutations can be introduced randomly along all or part of a CSAPL coding sequence, such as by saturation mutagenesis, and the resultant mutants can be screened for CSAPL biological activity to identify mutants that retain activity. Following mutagenesis of SEQ ID NO:1, or SEQ ID NO:3, the encoded protein can be expressed recombinantly and the activity of the protein can be determined.

In a preferred embodiment, a mutant CSAPL protein can be assayed for the ability to (1) regulate the cell cycle, e.g., modulation of signal transduction, e.g., hydrolysis of phosphatidylinositol-4,5-bisphosphate (PIP2) to release the second messengers 1,2-diacylglycerol (DAG) (e.g., DAG activates protein kinase C (PKC)) and 1,4,5-inositol trisphosphate (IP3) (e.g., IP3 releases calcium from stores in the endoplasmic reticulum); (2) modulate the inflammatory response, e.g., hydrolysis of the 2-acyl bond of 3-n-phosphoglycerides to produce arachidonic acid which is then processed into other molecules, e.g., leukotriens, which mediate the induction of the inflammatory response.

In addition to the nucleic acid molecules encoding CSAPL proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CSAPL coding strand, or to only a portion thereof. In one embodiment, an antisense nucleic acid molecule is antisense to a "coding region" of the coding strand of a nucleotide sequence encoding CSAPL. The term "coding region" refers to the region of the nucleotide sequence comprising codons which are translated into amino acid residues (e.g., the coding region of human CSAPL corresponds to). In another embodiment, the antisense nucleic acid molecule is antisense to a "noncoding region" of the coding strand of a nucleotide sequence encoding CSAPL. The term "noncoding region" refers to 5' and 3' sequences which flank the coding region that are not translated into amino acids (i.e., also referred to as 5' and 3' untranslated regions).

Given the coding strand sequences encoding CSAPL disclosed herein (e.g., SEQ ID NO:3), antisense nucleic acids of the invention can be designed according to the rules of Watson and Crick base pairing. The antisense nucleic acid molecule can be complementary to the entire coding region of CSAPL mRNA, but more preferably is an oligonucleotide which is antisense to only a portion of the coding or noncoding region of CSAPL mRNA. For example, the antisense oligonucleotide can be complementary to the region surrounding the translation start site of CSAPL mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CSAPL protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave CSAPL mRNA transcripts to thereby inhibit translation of CSAPL mRNA. A ribozyme having specificity for a CSAPL-encoding nucleic acid can be designed based upon the nucleotide sequence of a CSAPL cDNA disclosed herein (i.e., SEQ ID NO:1, or SEQ ID NO:3. For example, a derivative of a Tetrahymena L-19 IVS RNA can be constructed in which the nucleotide sequence of the active site is complementary to the nucleotide sequence to be cleaved in a CSAPL-encoding mRNA. See, e.g., Cech et al. U.S. Pat. No. 4,987,071; and Cech et al. U.S. Pat. No. 5,116,742. Alternatively, CSAPL mRNA can be used to select a catalytic RNA having a specific ribonuclease activity from a pool of RNA molecules. See, e.g., Bartel, D. and Szostak, J. W. (1993) *Science* 261:1411–1418.

Alternatively, CSAPL gene expression can be inhibited by targeting nucleotide sequences complementary to the regulatory region of the CSAPL (e.g., the CSAPL promoter and/or enhancers) to form triple helical structures that prevent transcription of the CSAPL gene in target cells. See generally, Helene, C. (1991) *Anticancer Drug Des.* 6(6):569–84; Helene, C. et al. (1992) *Ann. N.Y. Acad Sci.* 660:27–36; and Maher, L. J. (1992) *Bioassays* 14(12):807–15.

In yet another embodiment, the CSAPL nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93: 14670–675.

PNAs of CSAPL nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of CSAPL nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of CSAPL can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of CSAPL nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. W089/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated CSAPL Proteins and Anti-CSAPL Antibodies

One aspect of the invention pertains to isolated CSAPL proteins, and biologically active portions thereof, as well as polypeptide fragments suitable for use as immunogens to raise anti-CSAPL antibodies. In one embodiment, native CSAPL proteins can be isolated from cells or tissue sources by an appropriate purification scheme using standard protein purification techniques. In another embodiment, CSAPL proteins are produced by recombinant DNA techniques. Alternative to recombinant expression, a CSAPL protein or polypeptide can be synthesized chemically using standard peptide synthesis techniques.

An "isolated" or "purified" protein or biologically active portion thereof is substantially free of cellular material or other contaminating proteins from the cell or tissue source from which the CSAPL protein is derived, or substantially free from chemical precursors or other chemicals when chemically synthesized. The language "substantially free of cellular material" includes preparations of CSAPL protein in which the protein is separated from cellular components of the cells from which it is isolated or recombinantly produced. In one embodiment, the language "substantially free of cellular material" includes preparations of CSAPL protein having less than about 30% (by dry weight) of non-CSAPL protein (also referred to herein as a "contaminating protein"), more preferably less than about 20% of non-CSAPL protein, still more preferably less than about 10% of non-CSAPL protein, and most preferably less than about 5% non-CSAPL protein. When the CSAPL protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CSAPL protein in which the protein is separated from chemical precursors or other chemicals which are involved in the synthesis of the protein. In one embodiment, the language "substantially free of chemical precursors or other chemicals" includes preparations of CSAPL protein having less than about 30% (by dry weight) of chemical precursors or non-CSAPL chemicals, more preferably less than about 20% chemical precursors or non-CSAPL chemicals, still more preferably less than about 10% chemical precursors or non-CSAPL chemicals, and most preferably less than about 5% chemical precursors or non-CSAPL chemicals.

Biologically active portions of a CSAPL protein include peptides comprising amino acid sequences sufficiently homologous to or derived from the amino acid sequence of the CSAPL protein, e.g., the amino acid sequence shown in SEQ ID NO:2, which include less amino acids than the full length CSAPL proteins, and exhibit at least one activity of a CSAPL protein. Typically, biologically active portions comprise a domain or motif with at least one activity of the CSAPL protein. A biologically active portion of a CSAPL protein can be a polypeptide which is, for example, 10, 25, 50, 100 or more amino acids in length.

It is to be understood that a preferred biologically active portion of a CSAPL protein of the present invention may contain at least one of the above-identified structural domains. A more preferred biologically active portion of a CSAPL protein may contain at least two of the above-identified structural domains. Moreover, other biologically active portions, in which other regions of the protein are deleted, can be prepared by recombinant techniques and evaluated for one or more of the functional activities of a native CSAPL protein.

In a preferred embodiment, the CSAPL protein has an amino acid sequence shown in SEQ ID NO:2. In other embodiments, the CSAPL protein is substantially homologous to SEQ ID NO:2, and retains the functional activity of the protein of SEQ ID NO:2, yet differs in amino acid sequence due to natural allelic variation or mutagenesis, as described in detail in subsection I above.

Accordingly, in another embodiment, the CSAPL protein is a protein which comprises an amino acid sequence at least about 10%, 15%, 20%, 25%, 30%, 35%, 40%, 45%, 50%, 55%, 60%, 65%, 70%, 75%, 80%, 85%, 90%, 95%, 98%, 99%, or more homologous to the amino acid sequence of SEQ ID NO:2, and retains the functional activity of the CSAPL proteins of SEQ ID NO:2. Preferably, the protein is at least about 10–15% to SEQ ID NO:2, more preferably at least about 15–20% to SEQ ID NO:2, more preferably at least about 20–25% to SEQ ID NO:2, more preferably at least about 25–30% to SEQ ID NO:2, more preferably at least about 30–35% homologous to SEQ ID NO:2, more preferably at least about 35–40% homologous to SEQ ID NO:2, even more preferably at least about 40–45% homologous to SEQ ID NO:2, and even more preferably at least about 10–15%, 15–20%, 20–25%, 25–30%, 30–35%, 35–40%, 40–45%, 45–50%, 50–55%, 55–60%, 60–65%, 65–70%, 70–75%, 75–80%, 80–85%, 85–90%, or 90–95% or more homologous to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the CSAPL amino acid sequence of SEQ ID NO:2 having 197 amino acid residues, at least 100, preferably at least 120, more preferably at least 140, even more preferably at least 160, and even more preferably at least 170, 180, 190 or 200 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4:11–17 (1988) which has been incorporated into the ALIGN program (version 2.0) (available at http://vega.igh.cnrs.fr/bin/align-guess.cgi), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to CSAPL nucleic acid molecules of the invention. BLAST protein searches can be performed with the XBLAST program, score=50, wordlength=3 to obtain amino acid sequences homologous to CSAPL protein molecules of the invention. To obtain gapped alignments for comparison purposes, Gapped BLAST can be utilized as described in Altschul et al., (1997) *Nucleic Acids Res.* 25(17) :3389–3402. When utilizing BLAST and Gapped BLAST programs, the default parameters of the respective programs (e.g., XBLAST and NBLAST) can be used. See http://www.ncbi.nlm.nih.gov.

The invention also provides CSAPL chimeric or fusion proteins. As used herein, a CSAPL "chimeric protein" or "fusion protein" comprises a CSAPL polypeptide operatively linked to a non-CSAPL polypeptide. A "CSAPL polypeptide" refers to a polypeptide having an amino acid sequence corresponding to CSAPL, whereas a "non-CSAPL polypeptide" refers to a polypeptide having an amino acid sequence corresponding to a protein which is not substantially homologous to the CSAPL protein, e.g., a protein which is different from the CSAPL protein and which is derived from the same or a different organism. Within a CSAPL fusion protein the CSAPL polypeptide can correspond to all or a portion of a CSAPL protein. In a preferred embodiment, a CSAPL fusion protein comprises at least one biologically active portion of a CSAPL protein. In another preferred embodiment, a CSAPL fusion protein comprises at least two biologically active portions of a CSAPL protein. Within the fusion protein, the term "operatively linked" is intended to indicate that the CSAPL polypeptide and the non-CSAPL polypeptide are fused in-frame to each other. The non-CSAPL polypeptide can be fused to the N-terminus or C-terminus of the CSAPL polypeptide.

For example, in one embodiment, the fusion protein is a GST-CSAPL fusion protein in which the CSAPL sequences are fused to the C-terminus of the GST sequences. Such fusion proteins can facilitate the purification of recombinant CSAPL.

In another embodiment, the fusion protein is a CSAPL protein containing a heterologous signal sequence at its N-terminus. For example, the native CSAPL signal sequence can be removed and replaced with a signal sequence from another protein. In certain host cells (e.g., mammalian host cells), expression and/or secretion of CSAPL can be increased through use of a heterologous signal sequence.

The CSAPL fusion proteins of the invention can be incorporated into pharmaceutical compositions and administered to a subject in vivo. The CSAPL fusion proteins can be used to affect the bioavailability of a CSAPL target molecule. Use of CSAPL fusion proteins may be useful therapeutically for the treatment of lipid metabolism disorders (e.g., skin inflammation). Moreover, the CSAPL-fusion proteins of the invention can be used as immunogens to produce anti-CSAPL antibodies in a subject, to purify CSAPL ligands and in screening assays to identify molecules which inhibit the interaction of CSAPL with a CSAPL target molecule.

Preferably, a CSAPL chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termnini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A CSAPL-encoding nucleic acid can be cloned into such an expression vector such that the fusion moiety is linked in-frame to the CSAPL protein.

The present invention also pertains to variants of the CSAPL proteins which function as either CSAPL agonists (mimetics) or as CSAPL antagonists. Variants of the CSAPL proteins can be generated by mutagenesis, e.g., discrete point mutation or truncation of a CSAPL protein. An agonist of the CSAPL proteins can retain substantially the same, or a subset, of the biological activities of the naturally occurring form of a CSAPL protein. An antagonist of a CSAPL protein can inhibit one or more of the activities of the naturally occurring form of the CSAPL protein by, for example, competitively inhibiting the protease activity of a CSAPL protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the CSAPL protein.

In one embodiment, variants of a CSAPL protein which function as either CSAPL agonists (mimetics) or as CSAPL antagonists can be identified by screening combinatorial libraries of mutants, e.g., truncation mutants, of a CSAPL protein for CSAPL protein agonist or antagonist activity. In one embodiment, a variegated library of CSAPL variants is generated by combinatorial mutagenesis at the nucleic acid level and is encoded by a variegated gene library. A variegated library of CSAPL variants can be produced by, for example, enzymatically ligating a mixture of synthetic oligonucleotides into gene sequences such that a degenerate set of potential CSAPL sequences is expressible as individual polypeptides, or alternatively, as a set of larger fusion proteins (e.g., for phage display) containing the set of CSAPL sequences therein. There are a variety of methods which can be used to produce libraries of potential CSAPL variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CSAPL sequences. Methods for synthesizing degenerate oligonucleotides are known in the art (see, e.g., Narang, S. A. (1983) Tetrahedron 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CSAPL protein coding sequence can be used to generate a variegated population of CSAPL fragments for screening and subsequent selection of variants of a CSAPL protein. In one embodiment, a library of coding sequence fragments can be generated by treating a double stranded PCR fragment of a CSAPL coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, and internal fragments of various sizes of the CSAPL protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CSAPL proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify CSAPL variants (Arkin and Yourvan (1992) *PNAS* 89:7811–7815; Delgrave et al. (1993) *Protein Engineering* 6(3):327–331).

In one embodiment, cell based assays can be exploited to analyze a variegated CSAPL library. For example, a library of expression vectors can be transfected into a cell line which ordinarily synthesizes and secretes CSAPL. The transfected cells are then cultured such that CSAPL and a particular mutant CSAPL are secreted and the effect of expression of the mutant on CSAPL activity in cell supernatants can be detected, e.g., by any of a number of enzymatic assays. Plasmid DNA can then be recovered from the cells which score for inhibition, or alternatively, potentiation of CSAPL activity, and the individual clones further characterized.

An isolated CSAPL protein, or a portion or fragment thereof, can be used as an immunogen to generate antibodies that bind CSAPL using standard techniques for polyclonal and monoclonal antibody preparation. A full-length CSAPL protein can be used or, alternatively, the invention provides antigenic peptide fragments of CSAPL for use as immunogens. The antigenic peptide of CSAPL comprises at least 8 amino acid residues of the amino acid sequence shown in SEQ ID NO:2 and encompasses an epitope of CSAPL such that an antibody raised against the peptide forms a specific immune complex with CSAPL. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of CSAPL that are located on the surface of the protein, e.g., hydrophilic regions.

A CSAPL immunogen typically is used to prepare antibodies by immunizing a suitable subject, (e.g., rabbit, goat, mouse or other mammal) with the immunogen. An appropriate immunogenic preparation can contain, for example, recombinantly expressed CSAPL protein or a chemically synthesized CSAPL polypeptide. The preparation can firther include an adjuvant, such as Freund's complete or incomplete adjuvant, or similar immunostimulatory agent. Immunization of a suitable subject with an immunogenic CSAPL preparation induces a polyclonal anti-CSAPL antibody response.

Accordingly, another aspect of the invention pertains to anti-CSAPL antibodies. The term "antibody" as used herein refers to immunoglobulin molecules and immunologically active portions of immunoglobulin molecules, i.e., molecules that contain an antigen binding site which specifically binds (immunoreacts with) an antigen, such as CSAPL. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CSAPL. The term "monoclonal antibody" or "monoclonal antibody composition", as used herein, refers to a population of antibody molecules that contain only one species of an antigen binding site capable of immunoreacting with a particular epitope of CSAPL. A monoclonal antibody composition thus typically displays a single binding affinity for a particular CSAPL protein with which it imimunoreacts.

Polyclonal anti-CSAPL antibodies can be prepared as described above by immunizing a suitable subject with a CSAPL immunogen. The anti-CSAPL antibody titer in the immunized subject can be monitored over time by standard techniques, such as with an enzyme linked immunosorbent assay (ELISA) using immobilized CSAPL. If desired, the antibody molecules directed against CSAPL can be isolated from the mammal (e.g., from the blood) and further purified by well known techniques, such as protein A chromatography to obtain the IgG fraction. At an appropriate time after immunization, e.g., when the anti-CSAPL antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet*. 3:231–36). Briefly, an immortal cell line (typically a myeloma) is fused to lymphocytes (typically splenocytes) from a mammal immunized with a CSAPL immunogen as described above, and the culture supernatants of the resulting hybridoma cells are screened to identify a hybridoma producing a monoclonal antibody that binds CSAPL.

Any of the many well known protocols used for fusing lymphocytes and immortalized cell lines can be applied for the purpose of generating an anti-CSAPL monoclonal antibody (see, e.g., G. Galfre et al. (1977) *Nature* 266:55052; Gefter et al. *Somatic Cell Genet*., cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useflul. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CSAPL, e.g., using a standard ELISA assay.

Alternative to preparing monoclonal antibody-secreting hybridomas, a monoclonal anti-CSAPL antibody can be identified and isolated by screening a recombinant combinatorial immunoglobulin library (e.g., an antibody phage display library) with CSAPL to thereby isolate immunoglobulin library members that bind CSAPL. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-CSAPL antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173, 494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-CSAPL antibody (e.g., monoclonal antibody) can be used to isolate CSAPL by standard techniques, such as affinity chromatography or immunoprecipitation. An anti-CSAPL antibody can facilitate the purification of natural CSAPL from cells and of recombinantly produced CSAPL expressed in host cells. Moreover, an anti-CSAPL antibody can be used to detect CSAPL protein (e.g., in a cellular lysate or cell supernatant) in order to evaluate the abundance and pattern of expression of the CSAPL protein. Anti-CSAPL antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerytbrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a CSAPL protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequencers) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CSAPL proteins, mutant forms of CSAPL proteins, fusion proteins, etc.).

The recombinant expression vectors of the invention can be designed for expression of CSAPL proteins in prokaryotic or eukaryotic cells. For example, CSAPL proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in CSAPL activity assays, (e.g., direct assays or competitive assays described in detail below), or to generate antibodies specific for CSAPL proteins, for exanple. In a preferred embodiment, a CSAPL fusion protein expressed in a retroviral expression vector of the present invention can be utilized to infect bone marrow cells which are subsequently transplanted into irradiated recipients. The pathology of the subject recipient is then examined after sufficient time has passed (e.g six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the CSAPL expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, CSAPL proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CSAPL mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an CSAPL nucleic acid molecule of the invention is introduced, e.g., an CSAPL nucleic acid molecule within a recombinant expression vector or an CSAPL nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CSAPL protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a CSAPL protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CSAPL protein. Accordingly, the invention further provides methods for producing a CSAPL protein using the host cells of the invention. In one embodiment, the method comprises culturing the host cell of invention (into which a recombinant expression vector encoding a CSAPL protein has been introduced) in a suitable medium such that a CSAPL protein is produced. In another embodiment, the method further comprises isolating a CSAPL protein from the medium or the host cell.

The host cells of the invention can also be used to produce nonhuman transgenic animals. For example, in one embodiment, a host cell of the invention is a fertilized oocyte or an embryonic stem cell into which CSAPL-coding sequences have been introduced. Such host cells can then be used to create non-human transgenic animals in which exogenous CSAPL sequences have been introduced into their genome or homologous recombinant animals in which endogenous CSAPL sequences have been altered. Such animals are useful for studying the function and/or activity of a CSAPL and for identifying and/or evaluating modulators of CSAPL activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CSAPL gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a CSAPL-encoding nucleic acid into the male pronuclei of a fertilized oocyte, e.g., by microinjection, retroviral infection, and allowing the oocyte to develop in a pseudopregnant female foster animal. The CSAPL cDNA sequence of SEQ ID NO:1, SEQ ID NO:3 can be introduced as a transgene into the genome of a non-human animal. Alternatively, a nonhuman homologue of a human CSAPL gene, such as a mouse or rat CSAPL gene, can be used as a transgene. Alternatively, a CSAPL gene homologue, such as a CSAPL-2 gene can be isolated based on hybridization to the CSAPL cDNA sequences of SEQ ID NO:1, or SEQ ID NO:3 (described further in subsection I above) and used as a transgene. Intronic sequences and polyadenylation signals can also be included in the transgene to increase the efficiency of expression of the transgene. A tissue-specific regulatory sequence(s) can be operably linked to a CSAPL transgene to direct expression of a CSAPL protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a CSAPL transgene in its genome and/or expression of CSAPL mRNA in tissues or cells of the animals. A transgenic founder animal can then be used to breed additional animals carrying the transgene. Moreover, transgenic animals carrying a transgene encoding a CSAPL protein can further be bred to other transgenic animals carrying other transgenes.

To create a homologous recombinant animal, a vector is prepared which contains at least a portion of an CSAPL gene into which a deletion, addition or substitution has been introduced to thereby alter, e.g., functionally disrupt, the CSAPL gene. The CSAPL gene can be a human gene (e.g., the cDNA of SEQ ID NO:3), but more preferably, is a non-human homologue of a human CSAPL gene (e.g., a cDNA isolated by stringent hybridization with the nucleotide sequence of SEQ ID NO:1). For example, a mouse CSAPL gene can be used to construct a homologous recombination nucleic acid molecule, e.g., a vector, suitable for altering an endogenous CSAPL gene in the mouse genome. In a preferred embodiment, the homologous recombination nucleic acid molecule is designed such that, upon homologous recombination, the endogenous CSAPL gene is functionally disrupted (i.e., no longer encodes a functional protein; also referred to as a "knock out" vector). Alternatively, the homologous recombination nucleic acid molecule can be designed such that, upon homologous recombination, the endogenous CSAPL gene is mutated or otherwise altered but still encodes functional protein (e.g., the upstream regulatory region can be altered to thereby alter the expression of the endogenous CSAPL protein). In the homologous recombination nucleic acid molecule, the altered portion of the CSAPL gene is flanked at its 5' and 3' ends by additional nucleic acid sequence of the CSAPL gene to allow for homologous recombination to occur between the exogenous CSAPL gene carried by the homologous recombination nucleic acid molecule and an endogenous CSAPL gene in a cell, e.g., an embryonic stem cell. The additional flanking CSAPL nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced CSAPL gene has homologously recombined with the endogenous CSAPL gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_o$ phase. Alternatively, a cell, e.g., an embryonic stem cell, from the inner cell mass of a developing embryo can be transformed with a preferred transgene. Alternatively, a cell, e.g., a somatic cell, from cell culture line can be transformed with a preferred transgene and induced to exit the growth cycle and enter $G_o$ phase. The cell can then be fused, e.g., through the use of electrical pulses, to an enucleated mammalian oocyte. The reconstructed oocyte is then cultured such that it develops to morula or blastocyte and then transferred to pseudopregnant female foster animal. The offspring borne of this female foster animal will be a clone of the animal from which the nuclear donor cell, e.g., the somatic cell, is isolated.

IV. Pharmaceutical Compositions

The CSAPL nucleic acid molecules, CSAPL proteins, and anti-CSAPL antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermnal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CSAPL protein or anti-CSAPL antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

As described herein, a CSAPL protein of the invention has one or more of the following activities: (i) interaction of a CSAPL protein with a CSAPL target molecule; (ii) interaction of a CSAPL protein with a CSAPL target molecule, wherein the CSAPL target is a ligand, e.g., the 2-acyl bond of 3-n-phosphoglycerides.

Further as described herein, a CSAPL protein of the invention has one or more of the above activities and can thus be used in, for example, the: (1) regulation of cell cycle, e.g., modulation of signal transduction, e.g., hydrolysis of phosphatidylinositol-4,5-bisphosphate (PIP2) to release the second messengers 1,2-diacylglycerol (DAG) (e.g., DAG activates protein kinase C (PKC)) and 1,4,5-inositol trisphosphate (IP3) (e.g., IP3 releases calcium from stores in the endoplasmic reticulum); (2) modulation of the inflammatory response, e.g., hydrolysis of the 2-acyl bond of 3-n-phosphoglycerides to produce arachidonic acid which is then processed into other molecules, e.g., leukotriens, which mediate the induction of the inflammatory response.

The isolated nucleic acid molecules of the invention can be used, for example, to express CSAPL protein (e.g., via a recombinant expression vector in a host cell in gene therapy applications), to detect CSAPL mRNA (e.g., in a biological sample) or a genetic alteration in a CSAPL gene, and to modulate CSAPL activity, as described further below. The CSAPL proteins can be used to treat disorders characterized by insufficient or excessive production of a CSAPL or CSAPL target molecules. In addition, the CSAPL proteins can be used to screen for naturally occurring CSAPL target molecules, to screen for drugs or compounds which modulate CSAPL activity, as well as to treat disorders characterized by insufficient or excessive production of CSAPL protein or production of CSAPL protein forms which have decreased or aberrant activity compared to CSAPL wild type protein. Moreover, the anti-CSAPL antibodies of the invention can be used to detect and isolate CSAPL proteins, regulate the bioavailability of CSAPL proteins, and modulate CSAPL activity.

Accordingly one embodiment of the present invention involves a method of use (e.g., a diagnostic assay, prognostic assay, or a prophylactic/therapeutic method of treatment) wherein a molecule of the present invention (e.g., a CSAPL protein, CSAPL nucleic acid, or a CSAPL modulator) is used, for example, to diagnose, prognose and/or treat a disease and/or condition in which any of the aforementioned activities (i.e., activities (i)–(ii) and (1)–(2) in the above paragraph) is indicated. In another embodiment, the present invention involves a method of use (e.g., a diagnostic assay, prognostic assay, or a prophylacticltherapeutic method of treatment) wherein a molecule of the present invention (e.g., a CSAPL protein, CSAPL nucleic acid, or a CSAPL modulator) is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/therapeutic methods of treatment) involve administering to a subject, preferably a human subject, a molecule of the present invention (e.g., a CSAPL protein, CSAPL nucleic acid, or a CSAPL modulator) for the diagnosis, prognosis, and/or therapeutic treatment. In another embodiment, the methods of use (e.g., diagnostic assays, prognostic assays, or prophylactic/therapeutic methods of treatment) involve administering to a human subject a molecule of the present invention (e.g., a CSAPL protein, CSAPL nucleic acid, or a CSAPL modulator).

A. Screening Assays:

The invention provides a method (also referred to herein as a "screening assay") for identifying modulators, i.e., candidate or test compounds or agents (e.g., peptides, peptidomimetics, small molecules or other drugs) which bind to CSAPL proteins, have a stimulatory or inhibitory effect on, for example, CSAPL expression or CSAPL activity, or have a stimulatory or inhibitory effect on, for example, the activity of an CSAPL target molecule.

In one embodiment, the invention provides assays for screening candidate or test compounds which are target molecules of a CSAPL protein or polypeptide or biologically active portion thereof. In another embodiment, the invention provides assays for screening candidate or test compounds which bind to or modulate the activity of a CSAPL protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des*. 12:145).

Examples of methods for the synthesis of molecular libraries can be found in the art, for example in: DeWitt et al. (1993) *Proc. Natl. Acad. Sci U.S.A.* 90:6909; Erb et al. (1994) *Proc. Natl. Acad. Sci. USA* 91:11422; Zuckermann et al. (1994). *J. Med Chem*. 37:2678; Cho et al. (1993) *Science* 261:1303; Carrell et al. (1994) Angew. *Chem. Int. Ed. Engl*. 33:2059; Carell et al. (1994) Angew. Chem. Int. Ed. Engl. 33:2061; and in Gallop et al. (1994) *J. Med. Chem*. 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci*. 87:6378–6382); (Felici (1991) *J. Mol. Biol*. 222:301–310); (Ladner supra.).

In one embodiment, an assay is a cell-based assay in which a cell which expresses a CSAPL protein or biologically active portion thereof is contacted with a test compound and the ability of the test compound to modulate CSAPL activity determined. Determining the ability of the test compound to modulate CSAPL activity can be accomplished by monitoring the bioactivity of the CSAPL protein or biologically active portion thereof. The cell, for example, can be of mammalian origin or a yeast cell. Determining the ability of the test compound to modulate CSAPL activity can be accomplished, for example, by coupling the CSAPL protein or biologically active portion thereof with a radioisotope or enzymatic label such that binding of the CSAPL protein or biologically active portion thereof to its cognate target molecule can be determined by detecting the labeled CSAPL protein or biologically active portion thereof in a complex. For example, compounds (e.g., CSAPL protein or biologically active portion thereof) can be labeled with $^{125}I$, $^{35}S$, $^{14}C$, or $^3H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., CSAPL protein or biologically active portion thereof) to interact with its cognate target molecule without the labeling of any of the interactants. For example, a microphysiometer can be used to detect the interaction of a compound with its cognate target molecule without the labeling of either the compound or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which expresses a CSAPL protein or biologically active portion thereof, with a target molecule to form an assay mixture, contacting the assay mixture with a test compound, and determining the ability of the test compound to modulate the activity of the CSAPL protein or biologically active portion thereof, wherein determining the ability of the test compound to modulate the activity of the CSAPL protein or biologically active portion thereof, comprises determining the ability of the test compound to modulate a biological activity of the CSAPL expressing cell (e.g., determining the ability of the test compound to modulate lipid metabolism).

In another preferred embodiment, the assay comprises contacting a cell which is responsive to a CSAPL protein or biologically active portion thereof, with a CSAPL protein or biologically-active portion thereof, to form an assay mixture, contacting the assay mixture with a test compound, and determining the ability of the test compound to modulate the activity of the CSAPL protein or biologically active portion thereof, wherein determining the ability of the test compound to modulate the activity of the CSAPL protein or biologically active portion thereof comprises determining the ability of the test compound to modulate a biological activity of the CSAPL-responsive cell (e.g., determining the ability of the test compound to modulate lipid metabolism).

In another embodiment, an assay is a cell-based assay comprising contacting a cell expressing a CSAPL target molecule with a test compound and determining the ability of the test compound to modulate (e.g. stimulate or inhibit) the activity of the CSAPL target molecule. Determining the ability of the test compound to modulate the activity of a CSAPL target molecule can be accomplished, for example, by determining the ability of the CSAPL protein to bind to or interact with the CSAPL target molecule.

Determining the ability of the CSAPL protein to bind to or interact with a CSAPL target molecule can be accomplished by one of the methods described above for determining direct binding. In a preferred embodiment, determining the ability of the CSAPL protein to bind to or interact with a CSAPL target molecule can be accomplished by determining the activity of the target molecule. For example, the activity of the target molecule can be determined by detecting dephosphorylation of a phosphorylated protein. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response, for example, lipid metabolism.

In yet another embodiment, an assay of the present invention is a cell-free assay in which a CSAPL protein or biologically active portion thereof is contacted with a test compound and the ability of the test compound to bind to the CSAPL protein or biologically-active portion thereof is determined. Binding of the test compound to the CSAPL protein can be determined either directly or indirectly as described above. In a preferred embodiment, the assay includes contacting the CSAPL protein or biologically active portion thereof with a known compound which binds CSAPL (e.g., a CSAPL target molecule) to form an assay mixture, contacting the assay mixture with a test compound, and determining the ability of the test compound to interact with a CSAPL protein, wherein determining the ability of the test compound to interact with a CSAPL protein comprises determining the ability of the test compound to preferentially bind to CSAPL or biologically active portion thereof as compared to the known compound.

In another embodiment, the assay is a cell-free assay in which a CSAPL protein or biologically active portion thereof is contacted with a test compound and the ability of the test compound to modulate (e.g., stimulate or inhibit) the activity of the CSAPL protein or biologically active portion thereof is determined. Determining the ability of the test compound to modulate the activity of a CSAPL protein can be accomplished, for example, by determining the ability of the CSAPL protein to bind to a CSAPL target molecule by one of the methods described above for determining direct binding. Determining the ability of the CSAPL protein to bind to a CSAPL target molecule can also be accomplished using a technology such as real-time Biomolecular Interaction Analysis (BIA). Sjolander, S. and Urbaniczky, C. (1991) *Anal. Chem.* 63:2338–2345 and Szabo et al (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a CSAPL protein can be accomplished by determining the ability of the CSAPL protein to further modulate the activity of a downstream effector (e.g., a transcriptionally activated immediate early response pathway component) of a CSAPL target molecule. For example, the activity of the effector molecule on an appropriate target can be determined or the binding of the effector to an appropriate target can be determined as previously described.

In yet another embodiment, the cell-free assay involves contacting a CSAPL protein or biologically active portion thereof with a known compound which binds the CSAPL protein to form an assay mixture, contacting the assay mixture with a test compound, and determining the ability of the test compound to interact with the CSAPL protein, wherein determining the ability of the test compound to interact with the CSAPL protein comprises determining the ability of the CSAPL protein to preferentially bind to or modulate the activity of a CSAPL target molecule.

The cell-free assays of the present invention are amenable to use of both soluble and/or membrane-bound forms of isolated proteins (e.g. CSAPL proteins or biologically active portions thereof or receptors to which CSAPL targets bind). In the case of cell-free assays in which a membrane-bound form of an isolated protein is used (e.g., a cell surface receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either CSAPL or its target molecule to facilitate separation of complexed from uncomplexed forms of one or both of the proteins, as well as to accommodate automation of the assay. Binding of a test compound to a CSAPL protein, or interaction of a CSAPL protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/CSAPL fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or CSAPL protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CSAPL binding or activity determined using standard techniques.

Other techniques for immobilizing proteins on matrices can also be used in the screening assays of the invention. For example, either a CSAPL protein or a CSAPL target molecule can be immobilized utilizing conjugation of biotin and streptavidin. Biotinylated CSAPL protein or target molecules can be prepared from biotin-NHS (N-hydroxysuccinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CSAPL protein or target molecules but which do not interfere with binding of the CSAPL protein to its target molecule can be derivatized to the wells of the plate, and unbound target or CSAPL protein trapped in the wells by antibody conjugation. Methods for detecting such complexes, in addition to those described above for the GST-immobilized complexes, include immunodetection of complexes using antibodies reactive with the CSAPL protein or target molecule, as well as enzyme-linked assays which rely on detecting an enzymatic activity associated with the CSAPL protein or target molecule.

In another embodiment, modulators of CSAPL expression are identified in a method wherein a cell is contacted with a candidate compound and the expression of CSAPL mRNA or protein in the cell is determined. The level of expression of CSAPL mRNA or protein in the presence of the candidate compound is compared to the level of expression of CSAPL mRNA or protein in the absence of the candidate compound. The candidate compound can then be identified as a modulator of CSAPL expression based on this comparison. For example, when expression of CSAPL mRNA or protein is greater (statistically significantly greater) in the presence of the candidate compound than in its absence, the candidate compound is identified as a stimulator of CSAPL mRNA or protein expression. Alternatively, when expression of CSAPL mRNA or protein is less (statistically significantly less) in the presence of the candidate compound than in its absence, the candidate compound is identified as an inhibitor of CSAPL mRNA or protein expression. The level of CSAPL mRNA or protein expression in the cells can be determined by methods described herein for detecting CSAPL mRNA or protein.

In yet another aspect of the invention, the CSAPL proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with CSAPL ("CSAPL-binding proteins" or "CSAPL-bp") and are involved in CSAPL activity. Such CSAPL-binding proteins are also likely to be involved in the propagation of signals by the CSAPL proteins or CSAPL targets as, for example, downstream elements of a CSAPL-mediated signaling pathway. Alternatively, such CSAPL-binding proteins are likely to be CSAPL inhibitors.

The two-hybrid system is based on the modular nature of most transcription factors, which consist of separable DNA-binding and activation domains. Briefly, the assay utilizes two different DNA constructs. In one construct, the gene that codes for a CSAPL protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CSAPL-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the CSAPL protein.

This invention further pertains to novel agents identified by the above-described screening assays and to processes for producing such agents by use of these assays. Accordingly, in one embodiment, the present invention includes a compound or agent obtainable by a method comprising the steps of any one of the aformentioned screening assays (e.g., cell-based assays or cell-free assays). For example, in one embodiment, the invention includes a compound or agent obtainable by a method comprising contacting a cell which expresses a CSAPL target molecule with a test compound and the determining the ability of the test compound to bind to, or modulate the activity of, the CSAPL target molecule. In another embodiment, the invention includes a compound or agent obtainable by a method comprising contacting a cell which expresses a CSAPL target molecule with a CSAPL protein or biologically-active portion thereof, to form an assay mixture, contacting the assay mixture with a test compound, and determining the ability of the test compound to interact with, or modulate the activity of, the CSAPL target molecule. In another embodiment, the invention includes a compound or agent obtainable by a method comprising contacting a CSAPL protein or biologically active portion thereof with a test compound and determining the ability of the test compound to bind to, or modulate (e.g., stimulate or inhibit) the activity of, the CSAPL protein or biologically active portion thereof. In yet another embodiment, the present invention included a compound or agent obtainable by a method comprising contacting a CSAPL protein or biologically active portion thereof with a known compound which binds the CSAPL protein to form an assay mixture, contacting the assay mixture with a test compound, and determining the ability of the test compound to interact with, or modulate the activity of the CSAPL protein.

Accordingly, it is within the scope of this invention to further use an agent identified as described herein in an appropriate animal model. For example, an agent identified as described herein (e.g., a CSAPL modulating agent, an antisense CSAPL nucleic acid molecule, a CSAPL-specific antibody, or a CSAPL-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present inventon also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses a CSAPL target molecule is contacted with a test compound and the ability of the test compound to bind to, or modulate the activity of, the CSAPL target molecule is determined. In another exemplary embodiment, the present invention includes a method of synthesizing or producing a drug or pharmaceutical composition based on the structure and/or properties of a compound obtainable by a method in which a CSAPL protein or biologically active portion thereof is contacted with a test compound and the ability of the test compound to bind to, or modulate (e.g., stimulate or inhibit) the activity of, the CSAPL protein or biologically active portion thereof is determined.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the CSAPL nucleotide sequences, described herein, can be used to map the location of the CSAPL genes on a chromosome. The mapping of the CSAPL sequences to chromosomes is an important first step in correlating these sequences with genes associated with disease.

Briefly, CSAPL genes can be mapped to chromosomes by preparing PCR primers (preferably 15–25 bp in length) from the CSAPL nucleotide sequences. Computer analysis of the CSAPL sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the CSAPL sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CSAPL nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the CSAPL gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CSAPL sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CSAPL nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CSAPL nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:3 can comfortably provide positive individual identification with a panel of perhaps 10 to 1,000 primers which each yield a noncoding amplified sequence of 100 bases. If predicted coding sequences, such as those in SEQ ID NO:1, SEQ ID NO:3 are used, a more appropriate number of primers for positive individual identification would be 500–2,000.

If a panel of reagents from CSAPL nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial CSAPL Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:3 are particularly appropriate for this use as greater numbers of polymorphisms occur in the noncoding regions, making it easier to differentiate individuals using this technique. Examples of polynucleotide reagents include the CSAPL nucleotide sequences or portions thereof, e.g., fragments derived from the noncoding regions of SEQ ID NO:1, SEQ ID NO:3 having a length of at least 20 bases, preferably at least 30 bases.

The CSAPL nucleotide sequences described herein can further be used to provide polynucleotide reagents, e-g., labeled or labelable probes which can be used in, for example, an in situ hybridization technique, to identify a specific tissue, e.g., brain tissue. This can be very usefull in cases where a forensic pathologist is presented with a tissue of unknown origin. Panels of such CSAPL probes can be used to identify tissue by species and/or by organ type.

In a similar fashion, these reagents, e.g., CSAPL primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining CSAPL protein and/or nucleic acid expression as well as CSAPL activity, in the context of a biological sample (e.g., blood, serum, cells, tissue) to thereby determine whether an individual is afflicted with a disease or disorder, or is at risk of developing a disorder, associated with aberrant CSAPL expression or activity. The invention also provides for prognostic (or predictive) assays for determining whether an individual is at risk of developing a disorder associated with CSAPL protein, nucleic acid expression or activity. For example, mutations in a CSAPL gene can be assayed in a biological sample. Such assays can be used for prognostic or predictive purpose to thereby phophylactically treat an individual prior to the onset of a disorder characterized by or associated with CSAPL protein, nucleic acid expression or activity.

Another aspect of the invention pertains to monitoring the influence of agents (e.g., drugs, compounds) on the expression or activity of CSAPL in clinical trials.

These and other agents are described in further detail in the following sections.

1. Diagnostic Assays

An exemplary method for detecting the presence or absence of CSAPL protein or nucleic acid in a biological sample involves obtaining a biological sample from a test subject and contacting the biological sample with a compound or an agent capable of detecting CSAPL protein or nucleic acid (e.g., mRNA, genomic DNA) that encodes CSAPL protein such that the presence of CSAPL protein or nucleic acid is detected in the biological sample. A preferred agent for detecting CSAPL mRNA or genomic DNA is a labeled nucleic acid probe capable of hybridizing to CSAPL mRNA or genomic DNA. The nucleic acid probe can be, for example, a full-length CSAPL nucleic acid, such as the nucleic acid of SEQ ID NO:1 (or that of SEQ ID NO:3, or a portion thereof), such as an oligonucleotide of at least 15, 30, 50, 100, 250 or 500 nucleotides in length and sufficient to specifically hybridize under stringent conditions to CSAPL mRNA or genomic DNA. Other suitable probes for use in the diagnostic assays of the invention are described herein.

A preferred agent for detecting CSAPL protein is an antibody capable of binding to CSAPL protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CSAPL mRNA, protein, or genomic DNA in a biological sample in vitro as well as in vivo. For example, in vitro techniques for detection of CSAPL mRNA include Northern hybridizations and in situ hybridizations. In vitro techniques for detection of CSAPL protein include enzyme linked immunosorbent assays (ELISAs), Western blots, immunoprecipitations and immunofluorescence. In vitro techniques for detection of CSAPL genomic DNA include Southern hybridizations. Furthermore, in vivo techniques for detection of CSAPL protein include introducing into a subject a labeled anti-CSAPL antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting CSAPL protein, mRNA, or genomic DNA, such that the presence of CSAPL protein, mRNA or genomic DNA is detected in the biological sample, and comparing the presence of CSAPL protein, mRNA or genomic DNA in the control sample with the presence of CSAPL protein, mRNA or genomic DNA in the test sample.

The invention also encompasses kits for detecting the presence of CSAPL in a biological sample. For example, the kit can comprise a labeled compound or agent capable of detecting CSAPL protein or mRNA in a biological sample; means for determining the amount of CSAPL in the sample; and means for comparing the amount of CSAPL in the sample with a standard. The compound or agent can be packaged in a suitable container. The kit can further comprise instructions for using the kit to detect CSAPL protein or nucleic acid.

2. Prognostic Assays

The diagnostic methods described herein can furthermore be utilized to identify subjects having or at risk of developing a disease or disorder associated with aberrant CSAPL expression or activity. As used herein, the term "aberrant" includes an CSAPL expression or activity which deviates from the wild type CSAPL expression or activity. Aberrant expression or activity includes increased or decreased expression or activity, as well as expression or activity which does not follow the wild type developmental pattern of expression or the subcellular pattern of expression. For example, aberrant CSAPL expression or activity is intended to include the cases in which a mutation in the CSAPL gene causes the CSAPL gene to be under-expressed or over-expressed and situations in which such mutations result in a non-fimctional CSAPL protein or a protein which does not function in a wild-type fashion, e.g., a protein which does not interact with an CSAPL ligand or one which interacts with a non-CSAPL ligand.

The assays described herein, such as the preceding diagnostic assays or the following assays, can be utilized to identify subjects having or at risk of developing a disease or disorder associated with aberrant CSAPL expression or activity. For example, the assays described herein, such as the preceding diagnostic assays or the following assays, can be utilized to identify a subject having or at risk of developing a disorder associated with CSAPL protein, nucleic acid expression or activity such a lipid metabolism disorder (e.g., inflammation). Alternatively, the prognostic assays can be utilized to identify a subject having or at risk for developing a metabolic disorder. Thus, the present invention provides a method for identifying a disease or disorder associated with aberrant CSAPL expression or activity in which a test sample is obtained from a subject and CSAPL protein or nucleic acid (e.g, mRNA, genomic DNA) is detected, wherein the presence of CSAPL protein or nucleic acid is diagnostic for a subject having or at risk of developing a disease or disorder associated with aberrant CSAPL expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CSAPL expression or activity. For example, such methods can be used to determine whether a subject can be effectively treated with an agent fora lipid metabolism disorder (e.g., inflammation). For example, such methods can be used to determine whether a subject can be effectively treated with an agent for a metabolic disorder. Thus, the present invention provides methods for determining whether a subject can be effectively treated with an agent for a disorder associated with aberrant CSAPL expression or activity in which a test sample is obtained and CSAPL protein or nucleic acid expression or activity is detected (e.g., wherein the abundance of CSAPL protein or nucleic acid expression or activity is diagnostic for a subject that can be administered the agent to treat a disorder associated with aberrant CSAPL expression or activity.)

The methods of the invention can also be used to detect genetic alterations in a CSAPL gene, thereby determining if a subject with the altered gene is at risk for a disorder characterized by aberrant developmental progression. In preferred embodiments, the methods include detecting, in a sample of cells from the subject, the presence or absence of a genetic alteration characterized by at least one of an alteration affecting the integrity of a gene encoding a CSAPL-protein, or the mis-expression of the CSAPL gene. For example, such genetic alterations can be detected by ascertaining the existence of at least one of 1) a deletion of one or more nucleotides from a CSAPL gene; 2) an addition of one or more nucleotides to a CSAPL gene; 3) a substitution of one or more nucleotides of a CSAPL gene, 4) a chromosomal rearrangement of a CSAPL gene; 5) an alteration in the level of a messenger RNA transcript of a CSAPL gene, 6) aberrant modification of a CSAPL gene, such as of the methylation pattern of the genomic DNA, 7) the presence of a non-wild type splicing pattern of a messenger RNA transcript of a CSAPL gene, 8) a non-wild type level of a CSAPL-protein, 9) allelic loss of a CSAPL gene, and 10) inappropriate post-translational modification of a CSAPL-protein. As described herein, there are a large number of assay techniques known in the art which can be used for detecting alterations in a CSAPL gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the CSAPL-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CSAPL gene under conditions such that hybridization and amplification of the CSAPL-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially usefuil for the detection of nucleic acid molecules if such molecules are present in very low numbers.

In an alternative embodiment, mutations in a CSAPL gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in CSAPL can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in CSAPL can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CSAPL gene and detect mutations by comparing the sequence of the sample CSAPL with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/1610 1; Cohen et al. (1996) *Adv. Chromatogr.* 36:127–162; and Griffin et al. (1993) *Appl. Biochem. Biotechnol.* 38:147–159).

Other methods for detecting mutations in the CSAPL gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type CSAPL sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl Acad Sci USA 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CSAPL cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a CSAPL sequence, e.g., a wild-type CSAPL sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CSAPL genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat Res* 285:125–144; and Hayashi (1992) *Genet Anal Tech Appl* 9:73–79). Single-stranded DNA fragments of sample and control CSAPL nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e g, in clinical settings to diagnose patients exhibiting symptoms or family history of a disease or illness involving a CSAPL gene.

Furthermore, any cell type or tissue in which CSAPL is expressed may be utilized in the prognostic assays described herein.

3. Monitoring of Effects During Clinical Trials

Monitoring the influence of agents (e.g., drugs, compounds) on the expression or activity of a CSAPL protein (e.g., modulation of lipid metabolism, e.g., production of arachidonic acid) can be applied not only in basic drug screening, but also in clinical trials. For example, the effectiveness of an agent determined by a screening assay as described herein to increase CSAPL gene expression, protein levels, or upregulate CSAPL activity, can be monitored in clinical trials of subjects exhibiting decreased CSAPL gene expression, protein levels, or downregulated CSAPL activity. Alternatively, the effectiveness of an agent determined by a screening assay to decrease CSAPL gene expression, protein levels, or downregulate CSAPL activity, can be monitored in clinical trials of subjects exhibiting increased CSAPL gene expression, protein levels, or upregulated CSAPL activity. In such clinical trials, the expression or activity of a CSAPL gene, and preferably, other genes that have been implicated in, for example, a developmental disorder can be used as a "read out" or markers of the phenotype of a particular cell.

For example, and not by way of limitation, genes, including CSAPL, that are modulated in cells by treatment with an agent (e.g., compound, drug or small molecule) which modulates CSAPL activity (e.g., identified in a screening assay as described herein) can be identified. Thus, to study the effect of agents on proliferative disorders, for example, in a clinical trial, cells can be isolated and RNA prepared and analyzed for the levels of expression of CSAPL and other genes implicated in a proliferative or metabolic disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CSAPL or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CSAPL protein, mRNA, or genomic DNA in the preadministration sample; (iii) obtaining one or more post-administration samples from the subject; (iv) detecting the level of expression or activity of the CSAPL protein, mRNA, or genomic DNA in the post-administration samples; (v) comparing the level of expression or activity of the CSAPL protein, mRNA, or genomic DNA in the pre-administration sample with the CSAPL protein, mRNA, or genomic DNA in the post administration sample or samples; and (vi) altering the administration of the agent to the subject accordingly. For example, increased administration of the agent may be desirable to increase the expression or activity of CSAPL to higher levels than detected, i.e., to increase the effectiveness of the agent. Alternatively, decreased administration of the agent may be desirable to decrease expression or activity of CSAPL to lower levels than detected, i.e. to decrease the effectiveness of the agent. According to such an embodiment, CSAPL expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant CSAPL expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the CSAPL molecules of the present invention or CSAPL modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant CSAPL expression or activity, by administering to the subject a CSAPL or an agent which modulates CSAPL expression or at least one CSAPL activity. Subjects at risk for a disease which is caused or contributed to by aberrant CSAPL expression or activity can be identified by, for example, any or a combination of diagnostic or prognostic assays as described herein. Administration of a prophylactic agent can occur prior to the manifestation of symptoms characteristic of the CSAPL aberrancy, such that a disease or disorder is prevented or, alternatively, delayed in its progression. Depending on the type of CSAPL aberrancy, for example, a CSAPL, CSAPL agonist or CSAPL antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating CSAPL expression or activity for therapeutic purposes. Accordingly, in an exemplary embodiment, the modulatory method of the invention involves contacting a cell with a CSAPL or agent that modulates one or more of the activities of CSAPL protein activity associated with the cell. An agent that modulates CSAPL protein activity can be an agent as described herein, such as a nucleic acid or a protein, a naturally-occurring target molecule of a CSAPL protein, a CSAPL antibody, a CSAPL agonist or antagonist, a peptidomimetic of a CSAPL agonist or antagonist, or other small molecule. In one embodiment, the agent stimulates one or more CSAPL activities. Examples of such stimulatory agents include active CSAPL protein and a nucleic acid molecule encoding CSAPL that has been introduced into the cell. In another embodiment, the agent inhibits one or more CSAPL activites. Examples of such inhibitory agents include antisense CSAPL nucleic acid molecules, anti-CSAPL antibodies, and CSAPL inhibitors. These modulatory methods can be performed in vitro (e.g., by culturing the cell with the agent), in vivo (e.g, by administering the agent to a subject), or alternatively in situ (e.g., at the site of lesion or injury). As such, the present invention provides methods of treating an individual afflicted with a disease or disorder characterized by aberrant expression or activity of a CSAPL protein or nucleic acid molecule. In one embodiment, the method involves administering an agent (e.g., an agent identified by a screening assay described herein), or combination of agents that modulates (e.g., upregulates or downregulates) CSAPL expression or activity. In another embodiment, the method involves administering a CSAPL protein or nucleic acid molecule as therapy to compensate for reduced or aberrant CSAPL expression or activity.

Stimulation of CSAPL activity is desirable in situations in which CSAPL is abnormally downregulated and/or in which increased CSAPL activity is likely to have a beneficial effect. For example, stimulation of CSAPL activity is desirable in situations in which a CSAPL is downregulated and/or in which increased CSAPL activity is likely to have a beneficial effect. Likewise, inhibition of CSAPL activity is desirable in situations in which CSAPL is abnormally upregulated and/or in which decreased CSAPL activity is likely to have a beneficial effect.

3. Pharmacogenomics

The CSAPL molecules of the present invention, as well as agents, or modulators which have a stimulatory or inhibitory effect on CSAPL activity (e.g., CSAPL gene expression) as identified by a screening assay described herein can be administered to individuals to treat (prophylactically or therapeutically) immune disorders associated with aberrant CSAPL activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a CSAPL molecule or CSAPL modulator as well as tailoring the dosage and/or therapeutic regimen of treatment with a CSAPL molecule or CSAPL modulator.

Pharmacogenomics deals with clinically significant hereditary variations in the response to drugs due to altered drug disposition and abnormal action in affected persons. See e.g., Eichelbaum, M., *Clin Exp Pharmacol Physiol*, 1996, 23(10–11):983–985 and Linder, M. W., Clin Chem, 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a CSAPL protein or CSAPL receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a CSAPL molecule or CSAPL modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a CSAPL molecule or CSAPL modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of Human CSAPL cDNA

In this example, the identification and characterization of the gene encoding human CSAPL (also referred to as fchrb018a01) is described.

Isolation of the human CSAPL cDNA

The invention is based, at least in part, on the discovery of the human gene encoding CSAPL. The human CSAPL was isolated from a cDNA library which was prepared from tissue obtained from subjects suffering from congestive heart failure of ischemic and idiopathic origin. Briefly, a cardiac tissue sample was obtained from a biopsy of a patient suffering from congestive heart failure. mRNA was isolated from the cardiac tissue and a cDNA library was prepared therefrom using art known methods (described in, for example, *Molecular Cloning A Laboratory Manual*, 2nd Ed., ed. by Sambrook, Fritsch and Maniatis (Cold Spring Harbor Laboratory Press: 1989). Positive clones were isolated either by examining the top protein blast hit for each sequence, by blasting the libraries against known phospholipases, or by using a computer program that recognizes protein motifs of phospholipases.

The sequence of the positive clone was determined and found to contain an open reading frame. The nucleotide sequence encoding the human CSAPL protein is shown in FIG. 1 and are set forth as SEQ ID NO:1. The full length protein encoded by this nucleic acid comprises about 197 amino acids, and has the amino acid sequence shown in FIG. 1 and set forth as SEQ ID NO:2. The coding region (open reading frame) of SEQ ID NO:1 is set forth as SEQ ID NO:3.

Analysis of human CSAPL

A BLAST search (Altschul et al. (1990) *J. Mol. Biol.* 215:403) of the nucleotide and protein sequences of human CSAPL revealed that CSAPL is similar to the following protein: human dual specificity protein phosphatase 3 (Accession No. P51452). This protein is approximately 37.3% identical (over CSAPL amino acids 1–199) at the amino acid level. This alignment were generated utilizing the ALIGN program with the following parameter setting: PAM120, gap penalties: −12/−4 (Myers, E. and Miller, W. (1988) "Optimal Alignments in Linear Space" CABIOS 4:11–17).

Tissue Distribution of CSAPL mRNA

This Example describes the tissue distribution of CSAPL mRNA, as determined by Northern blot hybridization.

Northern blot hybridization with the RNA sample was performed under standard conditions and washed under stringent conditions, i.e., 0.2×SSC at 65° C. A DNA probe corresponding to fchrb018a01 was used. The DNA was radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations.

CSAPL message was detected in human heart and skeletal, in several rat tissues but predominantly in rat brain.

Example 2

Expression of Recombinant CSAPL Protein in Bacterial Cells

In this example, CSAPL is expressed as a recombinant glutathione-S-transferase (GST) fusion polypeptide in *E. coil* and the fusion polypeptide is isolated and characterized. Specifically, CSAPL is fused to GST and this fusion polypeptide is expressed in *E. coli*, e.g., strain PEB199. Expression of the GST-CSAPL fuision protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant CSAPL Protein in COS Cells

To express the CSAPL gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire CSAPL protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the CSAPL DNA sequence is amplified by PCR using two primers. The 5' primer contains the restriction site of interest followed by approximately twenty nucleotides of the CSAPL coding sequence starting from the initiation codon; the 3' end sequence contains complementary sequences to the other restriction site of interest, a translation stop codon, the HA tag or FLAG tag and the last 20 nucleotides of the CSAPL coding sequence. The PCR amplified fragment and the pcDNA/Amp vector are digested with the appropriate restriction enzymes and the vector is dephosphorylated using the ClAP enzyme (New England Biolabs, Beverly, Mass.). Preferably the two restriction sites chosen are different so that the CSAPL gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the CSAPL-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989. The expression of the CSAPL polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the CSAPL coding sequence is cloned directly into the polylinker of the pcDNA/Amp vector using the appropriate restriction sites. The resulting plasmid is transfected into COS cells in the manner described above, and the expression of the CSAPL polypeptide is detected by radiolabelling and immunoprecipitation using a CSAPL specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule selcted from the group consisting of:
   (a) an isolved nucleic acid molecule comprising the nucleotide sequence set forth in SEQ ID NO:1, or a complement thereof;
   (b) an isolated nucleic acid molecule comprising the nucleotide sequence set forth in SEQ ID NO:3, or a complement thereof;
   (c) an isolated nucleic acid molecule consisting of the nucleotide sequence set forth in SEQ ID NO:1, or a complement thereof;
   (d) an isolaed nucleic acid molecule consisting of the nucleotide sequence set forth in SEQ ID NO:3, or a complement thereof;
   (e) an isolated nucleic acid molecule which encodes a polypeptide comprising the amino acid sequence set forth in SEQ ID NO: 2, or a complement thereof;
   (f) an isolated nucleic acid molecule which encodes a polypeptide consisting of the amino acid sequence set forth in SEQ ID NO: 2, or a complement thereof;
   (g) an isolated nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1 or SEQ ID NO:3 at 6×SSC at 45° C., followed by one or more washes in 0.2×SSC, 0.1% SDS at 65° C.;
   (h) an isolated nucleic acid molecule comprising a nucleotide sequence which is at least 90% identical to the nucleotide squence of SEQ ID NO:1 or 3, or a complement thereof;
   (i) an isolated nucleic acid molecule consisting of a nucleotide sequence which is at least 90% identical to the nucleotide sequence of SEQ ID NO:1 or 3, or a complement thereof;
   (j) an isolated nucleic acid molecule which encodes a polypeptide comprising an amino acid sequence at least about 90% identical to the amino acid sequence of SEQ ID NO:2; and
   (k) an isolated nucleic acid molecule which encodes a polypeptide consisting of an amino acid sequence at least about 90% identical to the amino acid sequence of SEQ ID NO:2.

2. An isolated nucleic acid molecule comprising the nucleic acid molecule of claim 1, and a nucleotide sequence encoding a heterologous polypeptide.

3. A vector comprising the nucleic acid molecule of claim 1.

4. The vector of claim 3, which is an expression vector.

5. A vector comprising the nucleic acid molecule of claim 2.

6. The vector of claim 5, which is an expression vector.

7. A recombinant host cell comprising a nucleic acid molecule operatively linked to a recombinant regulatory sequences, said nucleic acid molecule selected from the group consisting of:
   (a) a nucleic acid moleclce comprising the nucleotide sequence set forth in SEQ ID NO:1, or a complement thereof;
   (b) a nucleic acid molecule comprising the nucleotide sequence set forth in SEQ ID NO:3, or a complement thereof;
   (c) a nucleic acid molecule consisting of the nucleotide sequence set forth in SEQ ID NO:1, or a complement thereof;
   (d) a nucleic acid molecule consisting of the nucleotide sequence set forth in SEQ ID NO:3, or a complement thereof;
   (e) a nucleic acid molecule which encodes a polypeptide comprising the amino acid sequence set forth in SEQ ID NO: 2, or a complement thereof;
   (f) a nucleic acid molecule which encodes a polypeptide consisting of the amino acid sequence set forth in SEQ ID NO: 2, or a complement thereof;
   (g) a nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1 or SEQ ID NO:3 at 6×SSC at 45° C., followed by one or more washes in 0.2×SSC, 0.1% SDS at 65° C.;
   (h) a nucleic acid molecule comprising a nucleotide sequence which is at least 90% identical to the nucleotide sequence of SEQ ID NO:1 or 3, or a complement thereof;
   (i) a nucleic acid molecule consisting of a nucleotide sequence which is at least 90% identical to the nucleotide sequence of SEQ ID NO:1 or 3, or a complement thereof;
   (j) a nucleic acid molecule which encodes a polypeptide comprising an amino acid sequence at least about 90% identical to the amino acid sequence of SEQ ID NO:2; and
   (k) a nucleic acid molecule which encodes a polypeptide consisting of an amino acid sequence at least about 90% identical to the amino acid sequence of SEQ ID NO:2.

8. A recombinant host cell comprising the nucleic acid of claim 2.

9. A method of expressing a polypeptide comprising the step of culturing the host cell of claim 7 under conditions in which the nucleic acid molecule is expressed, thereby expressing the polypeptide.

10. A method of producing a polypeptide comprising the step of culturing the host cell of claim 7 under conditions in which the nucleic acid molecule is expressed.

11. A method of expressing a polypeptide comprising the step of culturing the host cell of claim 8 under conditions in which the nucleic acid molecule is expressed, thereby expressing the polypeptide.

12. A method of producing a polypeptide comprising the step of culturing the host cell of claim 8 under conditions in which the nucleic acid is expressed.

13. A kit comprising the nucleic acid molecule of claim 1 and instructions for use.

14. A kit comprising the nucleic acid molecule of claim 2 and instructions for use.

* * * * *

UNITED STATES PATENT AND TRADEMARK OFFICE
CERTIFICATE OF CORRECTION

PATENT NO. : 6,268,135 B1
DATED : July 31, 2001
INVENTOR(S) : Susan Acton

Page 1 of 1

It is certified that error appears in the above-identified patent and that said Letters Patent is hereby corrected as shown below:

<u>Column 63,</u>
Line 2, delete "nuclcic" and insert -- nucleic --.
Line 2, delete "selcted" and insert -- selected --.
Line 4, delete "isolved" and insert -- isolated --.
Line 14, delete "isolaed" and insert -- isolated --.
Line 33, delete "squence" and insert -- sequence --.
Line 58, delete "sequences" and insert -- sequence --.
Line 60, delete "moleclce" and insert -- molecule --.

Signed and Sealed this

Twenty-eighth Day of May, 2002

Attest:

JAMES E. ROGAN
Attesting Officer     Director of the United States Patent and Trademark Office

SEQUENCE LISTING

```
<160> NUMBER OF SEQ ID NOS: 3

<210> SEQ ID NO 1
<211> LENGTH: 912
<212> TYPE: DNA
<213> ORGANISM: Homo sapiens
<220> FEATURE:
<221> NAME/KEY: CDS
<222> LOCATION: (52)..(645)

<400> SEQUENCE: 1
gtcgacccac gcgtccggaa gtgcacagcc tgggccagat actcccacag g atg gac        57
                                                         Met Asp
                                                         1 tca ctg cag aag cag gac ctc cgg agg ccc aag atc cat ggg gca gtc       105
Ser Leu Gln Lys Gln Asp Leu Arg Arg Pro Lys Ile His Gly Ala Val
      5                  10                  15 cag gca tct ccc tac cag ccg ccc aca ttg gct tcg ctg cag cgc ttg       153
Gln Ala Ser Pro Tyr Gln Pro Pro Thr Leu Ala Ser Leu Gln Arg Leu
  20                  25                  30 ctg tgg gtc cgt cag gct gcc aca ctg aac cat atc gat gag gtc tgg       201
Leu Trp Val Arg Gln Ala Ala Thr Leu Asn His Ile Asp Glu Val Trp
 35                  40                  45                  50 ccc agc ctc ttc ctg gga gat gcg tac gca gcc cgg gac aag agc aag       249
Pro Ser Leu Phe Leu Gly Asp Ala Tyr Ala Ala Arg Asp Lys Ser Lys
              55                  60                  65
```

```
ctg atc cag ctg gga atc acc cac gtt gtg aat gcc gct gca ggc aag    297
Leu Ile Gln Leu Gly Ile Thr His Val Val Asn Ala Ala Ala Gly Lys
             70                  75                  80 ttc cag gtg gac aca ggt gcc aaa ttc tac cgt gga atg tcc ctg gag    345
Phe Gln Val Asp Thr Gly Ala Lys Phe Tyr Arg Gly Met Ser Leu Glu
         85                  90                  95 tac tat ggc att gag gcg gac gac aac ccc ttc ttc gac ctc agt gtc    393
Tyr Tyr Gly Ile Glu Ala Asp Asp Asn Pro Phe Phe Asp Leu Ser Val
100                 105                 110 tac ttt ctg cct gtt gct cga tac atc cga gct gcc ctc agt gtt ccc    441
Tyr Phe Leu Pro Val Ala Arg Tyr Ile Arg Ala Ala Leu Ser Val Pro
115                 120                 125                 130 caa ggc cgc gtg ctg gta cac tgt gcc atg ggg gta agc cgc tct gcc    489
Gln Gly Arg Val Leu Val His Cys Ala Met Gly Val Ser Arg Ser Ala
                135                 140                 145 aca ctt gtc ctg gcc ttc ctc atg atc tat gag aac atg acg ctg gta    537
Thr Leu Val Leu Ala Phe Leu Met Ile Tyr Glu Asn Met Thr Leu Val
            150                 155                 160 gag gcc atc cag acg gtg cag gcc cac cgc aat atc tgc cct aac tca    585
Glu Ala Ile Gln Thr Val Gln Ala His Arg Asn Ile Cys Pro Asn Ser
        165                 170                 175 ggc ttc ctc cgg cag ctc cag gtt ctg gac aac cga ctg ggg cgg gag    633
Gly Phe Leu Arg Gln Leu Gln Val Leu Asp Asn Arg Leu Gly Arg Glu
    180                 185                 190 acg ggg cgg ttc tgatctggca ggcagccagg atccctgacc cttggcccaa        685
Thr Gly Arg Phe
195 ccccaccagc ctggccctgg aacagcagg ctctgctgtt tctagtgacc ctgagatgta    745 aacagcaagt gggggctgag gcagaggcag ggatagctgg gtggtgacct cttagcgggt    805 ggatttccct gacccaattc agagattctt tatgcaaaag tgagttcagt ccatctctat    865 aataaaatat tcatcgtcat aaaaaaaaaa aaaaaagggg cggccgc                 912

<210> SEQ ID NO 2
<211> LENGTH: 198
<212> TYPE: PRT
<213> ORGANISM: Homo sapiens

<400> SEQUENCE: 2

Met Asp Ser Leu Gln Lys Gln Asp Leu Arg Arg Pro Lys Ile His Gly
 1               5                  10                  15

Ala Val Gln Ala Ser Pro Tyr Gln Pro Pro Thr Leu Ala Ser Leu Gln
            20                  25                  30

Arg Leu Leu Trp Val Arg Gln Ala Ala Thr Leu Asn His Ile Asp Glu
        35                  40                  45

Val Trp Pro Ser Leu Phe Leu Gly Asp Ala Tyr Ala Ala Arg Asp Lys
    50                  55                  60

Ser Lys Leu Ile Gln Leu Gly Ile Thr His Val Val Asn Ala Ala Ala
65                  70                  75                  80

Gly Lys Phe Gln Val Asp Thr Gly Ala Lys Phe Tyr Arg Gly Met Ser
                85                  90                  95

Leu Glu Tyr Tyr Gly Ile Glu Ala Asp Asp Asn Pro Phe Phe Asp Leu
            100                 105                 110

Ser Val Tyr Phe Leu Pro Val Ala Arg Tyr Ile Arg Ala Ala Leu Ser
        115                 120                 125

Val Pro Gln Gly Arg Val Leu Val His Cys Ala Met Gly Val Ser Arg
    130                 135                 140
```

-continued

```
Ser Ala Thr Leu Val Leu Ala Phe Leu Met Ile Tyr Glu Asn Met Thr
145                 150                 155                 160

Leu Val Glu Ala Ile Gln Thr Val Gln Ala His Arg Asn Ile Cys Pro
                165                 170                 175

Asn Ser Gly Phe Leu Arg Gln Leu Gln Val Leu Asp Asn Arg Leu Gly
            180                 185                 190

Arg Glu Thr Gly Arg Phe
            195
```

<210> SEQ ID NO 3
<211> LENGTH: 594
<212> TYPE: DNA
<213> ORGANISM: Homo sapiens
<220> FEATURE:
<221> NAME/KEY: CDS
<222> LOCATION: (1)..(594)

<400> SEQUENCE: 3

```
atg gac tca ctg cag aag cag gac ctc cgg agg ccc aag atc cat ggg    48
Met Asp Ser Leu Gln Lys Gln Asp Leu Arg Arg Pro Lys Ile His Gly
1               5                   10                  15 gca gtc cag gca tct ccc tac cag ccg ccc aca ttg gct tcg ctg cag    96
Ala Val Gln Ala Ser Pro Tyr Gln Pro Pro Thr Leu Ala Ser Leu Gln
            20                  25                  30 cgc ttg ctg tgg gtc cgt cag gct gcc aca ctg aac cat atc gat gag   144
Arg Leu Leu Trp Val Arg Gln Ala Ala Thr Leu Asn His Ile Asp Glu
        35                  40                  45 gtc tgg ccc agc ctc ttc ctg gga gat gcg tac gca gcc cgg gac aag   192
Val Trp Pro Ser Leu Phe Leu Gly Asp Ala Tyr Ala Ala Arg Asp Lys
    50                  55                  60 agc aag ctg atc cag ctg gga atc acc cac gtt gtg aat gcc gct gca   240
Ser Lys Leu Ile Gln Leu Gly Ile Thr His Val Val Asn Ala Ala Ala
65                  70                  75                  80 ggc aag ttc cag gtg gac aca ggt gcc aaa ttc tac cgt gga atg tcc   288
Gly Lys Phe Gln Val Asp Thr Gly Ala Lys Phe Tyr Arg Gly Met Ser
                85                  90                  95 ctg gag tac tat ggc att gag gcg gac gac aac ccc ttc ttc gac ctc   336
Leu Glu Tyr Tyr Gly Ile Glu Ala Asp Asp Asn Pro Phe Phe Asp Leu
            100                 105                 110 agt gtc tac ttt ctg cct gtt gct cga tac atc cga gct gcc ctc agt   384
Ser Val Tyr Phe Leu Pro Val Ala Arg Tyr Ile Arg Ala Ala Leu Ser
        115                 120                 125 gtt ccc caa ggc cgc gtg ctg gta cac tgt gcc atg ggg gta agc cgc   432
Val Pro Gln Gly Arg Val Leu Val His Cys Ala Met Gly Val Ser Arg
    130                 135                 140 tct gcc aca ctt gtc ctg gcc ttc ctc atg atc tat gag aac atg acg   480
Ser Ala Thr Leu Val Leu Ala Phe Leu Met Ile Tyr Glu Asn Met Thr
145                 150                 155                 160 ctg gta gag gcc atc cag acg gtg cag gcc cac cgc aat atc tgc cct   528
Leu Val Glu Ala Ile Gln Thr Val Gln Ala His Arg Asn Ile Cys Pro
                165                 170                 175 aac tca ggc ttc ctc cgg cag ctc cag gtt ctg gac aac cga ctg ggg   576
Asn Ser Gly Phe Leu Arg Gln Leu Gln Val Leu Asp Asn Arg Leu Gly
            180                 185                 190 cgg gag acg ggg cgg ttc                                           594
Arg Glu Thr Gly Arg Phe
            195
```